US009561289B2

(12) United States Patent
Corti et al.

(10) Patent No.: US 9,561,289 B2
(45) Date of Patent: Feb. 7, 2017

(54) PEPTIDES FOR INHIBITING TUMOR GROWTH

(71) Applicant: OSPEDALE SAN RAFFAELE SRL, Milan (IT)

(72) Inventors: Angelo Corti, Milan (IT); Flavio Curnis, Milan (IT)

(73) Assignee: OSPEDALE SAN RAFFAELE SRL, Milan (IT)

( * ) Notice: Subject to any disclaimer, the term of this patent is extended or adjusted under 35 U.S.C. 154(b) by 0 days.

(21) Appl. No.: 14/386,415

(22) PCT Filed: Mar. 14, 2013

(86) PCT No.: PCT/IB2013/052040
§ 371 (c)(1),
(2) Date: Sep. 19, 2014

(87) PCT Pub. No.: WO2013/140317
PCT Pub. Date: Sep. 26, 2013

(65) Prior Publication Data
US 2015/0045302 A1 Feb. 12, 2015

(30) Foreign Application Priority Data
Mar. 20, 2012 (GB) .................................. 1204868.2

(51) Int. Cl.
*A61K 47/42* (2006.01)
*A61K 47/48* (2006.01)
*A61K 49/00* (2006.01)
*A61K 31/337* (2006.01)
*A61K 38/19* (2006.01)
*A61K 38/20* (2006.01)
*C07K 7/64* (2006.01)

(52) U.S. Cl.
CPC ....... *A61K 47/48284* (2013.01); *A61K 31/337* (2013.01); *A61K 38/191* (2013.01); *A61K 38/208* (2013.01); *A61K 47/48015* (2013.01); *A61K 47/48238* (2013.01); *A61K 47/48246* (2013.01); *A61K 49/0056* (2013.01); *A61K 49/0093* (2013.01); *C07K 7/64* (2013.01); *C07K 2319/31* (2013.01); *C07K 2319/33* (2013.01); *C07K 2319/74* (2013.01)

(58) Field of Classification Search
None
See application file for complete search history.

(56) References Cited

U.S. PATENT DOCUMENTS 7,795,386 B2 * 9/2010 Corti .............. A61K 47/48246 424/85.1
2003/0199043 A1 * 10/2003 Ballance .......... A61K 47/48338 435/69.7

FOREIGN PATENT DOCUMENTS

| WO | WO 98/17319 A2 | 4/1998 |
|---|---|---|
| WO | WO 99/24462 A2 | 5/1999 |
| WO | WO 2004/091551 A2 | 10/2004 |
| WO | WO 2005/035002 A1 | 4/2005 |
| WO | WO 2006/067633 A2 | 6/2006 |
| WO | WO 2009/070234 A2 | 6/2009 |

OTHER PUBLICATIONS

Andreas et al. "Conformational Control of Integrin-Subtype Selectivity in isoDGR Peptide Motifs: A Biological Switch," Angew. Chem. Int. Ed. 2010, 49, 9278-9281.*
Wang et al. "Development of NGR peptide-based agents for tumor imaging," Am J Nucl Med Mol Imaging 2011;1(1):36-46.*
Frank et al. "Conformational Control of Integrin-Subtype Selectivity in isoDGR Peptide Motifs: A Biological Switch" Angew. Chem. Int. Ed. 2010, 49, 9278-9281.*
Christian et al. "Particle-mediated delivery of cytokines for immunotherapy" Immunotherapy. Apr. 2012; 4(4): 425-441.*
Arosio et al. "Cyclic RGD Functionalized Gold Nanoparticles for Tumor Targeting" Bioconjugate Chemistry, 2011, 22, 664-672.*
Khullar et al. "Bovine Serum Albumin Bioconjugated Gold Nanoparticles: Synthesis, Hemolysis, and Cytotoxicity toward Cancer Cell Lines," J. Phys Chem C, 2012, 116, 8834-8843.*
Search Report prepared by the Great Britain Patent Office on Jul. 19, 2012, for Great Britain Application No. GB 1204868.2.
International Search Report prepared by the European Patent Office on Jun. 13, 2013, for International Application No. PCT/IB2013/052040.
Written Opinion prepared by the European Patent Office on Jun. 13, 2013, for International Application No. PCT/IB2013/052040.
Frank et al. "Conformational Control of Integrin-Subtype Selectivity in isoDGR Peptide Motifs: A Biological Switch", Angewandte Chemie International Edition, vol. 49, No. 48, Nov. 22, 2010, pp. 9278-9281.
Wang et al. "Development of NGR peptide-based agents for tumor imaging", American Journal of Nuclear Medicine and Molecular Imaging 2011, vol. 1, No. 1, 2011, pp. 36-46.
Holle et al. "In vitro targeted killing of human endothelial cells by co-incubation of human serum and NGR peptide conjugated human albumin protein bearing alpha (1-3) galactose epitopes", Oncology Reports, vol. 11, No. 3, Mar. 1, 2004, pp. 613-616.
Delforge et al. "Design of a synthetic adhesion protein by grafting RGD tailed cyclic peptides on bovine serum albumin", Letters in Peptide Science, Escom Science Publishers, NL, vol. 5, Jan. 1, 1998 (Jan. 1, 1998), pp. 87-91.
Temming et al. "RGD-based strategies for selective delivery of therapeutics and imaging agents to the tumour vasculature", Drug Resistance Updates, vol. 8, No. 6, Dec. 1, 2005, pp. 381-402.

(Continued)

*Primary Examiner* — Christina Bradley
(74) *Attorney, Agent, or Firm* — Sheridan Ross P.c.

(57) ABSTRACT

A product comprising a peptide that comprises a motif selected from a group consisting of isoDGR, NGR and DGR, wherein the peptide cyclized by joining the N- and C-termini of its main chain and wherein the cyclic peptide is joined to albumin.

12 Claims, 17 Drawing Sheets

(56) References Cited

OTHER PUBLICATIONS

Curnis et al. "IsoDGR-Tagged Albumin: A New [alpha]v[beta]3 Selective Carrier for Nanodrug Delivery to Tumors", SMALL, vol. 9, No. 5, Mar. 11, 2013, pp. 673-678.
Curnis et al. "Isoaspartate-glycine-arginine: A new tumor vasculature-targeting motif", Cancer Research, vol. 68, No. 17, Sep. 2008, pp. 7073-7082.
Curnis et al. "Critical Role of Flanking Residues in NGR-to-isoDGR Transition and CD13/Integrin Receptor Switching", The Journal of Biological Chemistry, vol. 285, No. 12, Mar. 2010, pp. 9114-9123.
Mingozzie et al, "Cyclic iso DGR Peptidomimetics as Low-Nanomolar [alpha] v [beta] 3 Integrin Ligands", Chemistry—A European Journal, vol. 19, No. 11, Mar. 11, 2013, pp. 3563-3567.
International Preliminary Report on Patentability for International (PCT) Application No. PCT/IB2013/052040, mailed Oct. 14, 2014, 12 pages.

\* cited by examiner

PEPTIDES FOR INHIBITING TUMOR GROWTH

CROSS REFERENCE TO RELATED APPLICATIONS

This application is a national stage application under 35 U.S.C. 371 and claims the benefit of PCT Application No. PCT/IB2013/052040 having an international filing date of Mar. 14, 2013, which designated the United States, which PCT application claimed the benefit of Great Britain Patent Application No. 1204868.2 filed Mar. 20, 2012, the disclosure of each of which are incorporated herein by reference.

REFERENCE TO SEQUENCE LISTING

This application contains a Sequence Listing submitted as an electronic text file named "2186OSR-1_Sequence_Listing_ST25.txt", having a size in bytes of 14 kb, and amended on Jul. 28, 2016. The information contained in this electronic file is hereby incorporated by reference in its entirety pursuant to 37 CFR §1.52(e)(5).

FIELD OF THE INVENTION

The present invention relates to novel peptides which may be used in the treatment of diseases associated with angiogenesis and cancer.

BACKGROUND TO THE INVENTION

Albumin is emerging as a versatile drug carrier in a number of applications in cancer nanomedicine. We coupled albumin with a peptide containing the isoDGR motif, a ligand of integrins expressed in tumor vessels, to enhance its tumor homing properties. To this aim, we designed various head-to-tail-cyclized isoDGR peptides and analyzed their integrin binding properties. We have identified a peptide (c(CGisoDGRG)) (SEQ ID NO:1) that, after coupling to human serum albumin, has a very good selectivity for $\alpha v\beta 3$ and $\alpha v\beta 5$, two integrins overexpressed in the tumor vasculature. In vitro and in vivo studies showed that isoDGR-tagged albumin binds to endothelial cells, inhibits their adhesion properties, homes in on tumor vessels and inhibits tumor growth, with no evidence of toxicity. Furthermore, coupling c(CGisoDGRG) (SEQ ID NO:1) to albumin/paclitaxel nanoparticles improved their cytotoxic activity against $\alpha v\beta 3$-positive endothelial cells, but not against $\alpha v\beta 3$-negative cells. These results suggest that isoDGR-tagged albumin is a new vascular targeting agent. Because of its good selectivity for tumor vessels and its inherent anticancer activity isoDGR-tagged albumin might be exploited as a carrier for the preparation of a wide range of tumor vasculature-selective drugs and nanoparticles for cancer therapy and diagnosis.

SUMMARY OF THE INVENTION

The invention describes a novel conjugable head-to-tail cyclized isoDGR compound (5 & 6 ring structures) containing the isoDGR motif (i.e. isoAsp-Gly-Arg), a ligand of integrins expressed in tumor vessels. Importantly, the cyclic isoDGR motif contains a free thiol group that enables peptide conjugation to several compounds such as human serum albumin, avidin and Qdot-fluorescent nanoparticles for drug delivery or diagnostic imaging.

In particular, the invention defines an isoDGR-tagged albumin, endowed of anti-tumor activity, which can be exploited for the preparation of tumor-homing nanoparticles.

From our prior art analysis, no cyclic CGisoDGRG (SEQ ID NO:1) peptides have been identified, therefore the invention is considered novel.

To our knowledge, integrin-selective cyclic iso-DG-peptides motifs so far developed (e.g., the CisoDGRC) (SEQ ID NO:2) do not contain functional groups that can be exploited for chemical coupling to any compound without causing loss of integrin-binding selectivity.

Moreover, the selectivity and the affinity of the modified compounds could not be predicted.

The inventors have:
  demonstrated that CGisoDGRG (SEQ ID NO:1) peptide (see structure in FIG. 1 below) is more stable, more selective towards $\alpha v\beta 3$ and easily conjugable compared to compounds already reported in the literature.
  a peptide to be chosen in order to synthesize any isoDGR-tagged compound such as isoDGR-nanoparticles or isoDGR-vasculature-selective drugs;
  data showing that the peptide is active after conjugation with human albumin (HSA), Qdot-fluorescent nanoparticles (Qdot) and Abraxane (Abx), in vitro and in vivo;
  data reporting how different the specificity and affinity of cyclic peptides are towards a number of integrins;
  the proposed cyclic peptide has got a good affinity and specificity towards integrins even compared to Cilengitide.
  Advantages over existing formulations include
  cyclic isoDGR peptide can be conjugated to anticancer agents, or to diagnostic compounds for in vivo imaging;
  considering that many groups throughout the world are trying to exploit Albumin (HSA) as a drug carrier, the isoDGR-tagged albumin can also be exploited for the preparation of tumor-homing therapeutic or diagnostic nanoparticles in place of albumin. Indeed, the improved tumor homing properties and anticancer activity of this conjugate, may represent a potential advantage.

It will be appreciated that the present invention can also encompass the motifs NGR and DGR.

STATEMENTS OF THE INVENTION

Aspects and embodiments of the invention will now be described with reference to the following numbers paragraphs:

1. A product comprising a peptide that comprises a motif selected from a group consisting of NGR, DGR and isoDGR, wherein the peptide is joined to albumin.
2. The product according to para 1 wherein the albumin is human serum albumin.
3. The product according to para 1 or 2 wherein the peptide is a cyclic peptide.
4. The product according to para 3 wherein the peptide is a cyclic hexapeptide.
5. The product according to para 3 wherein the peptide is a cyclic pentapeptide.
6. The product according to para 4 wherein the peptide comprises the sequence XX'isoDGRX" (SEQ ID NO:3), wherein X is selected from the group consisting of G, C and phG; X' is selected from the group consisting of G, C and phG; and X" is selected from the group consisting of G and phG. In one embodiment the isoDGR may be replaced with NGR, DGR orRGD.

7. The product according to any previous para wherein the peptide comprises an amino acid suitable for conjugation, in addition to the NGR, DGR or isoDGR motif.
8. The product according to para 7 wherein the amino acid suitable for conjugation can be conjugated via its side chain
9. The product according to para 8 wherein the amino acid suitable for conjugation via its side chain is selected from the group consisting of C, K and any non-standard amino acid that contains a free thiol or amine.
10. The product according to para 4 wherein the peptide comprises cyclic CGisoDGRG (SEQ ID NO:1), cyclic GCisoDGRG (SEQ ID NO:4), cyclic CphGisoDGRG (SEQ ID NO:5), cyclic CGisoDGRphG (SEQ ID NO:6), cyclic GCisoDGRphG (SEQ ID NO:7) or cyclic phGCisoDGRG (SEQ ID NO:8).
11. The product according to para 5 wherein the peptide comprises cyclic CisoDGRG (SEQ ID NO:9).
12. The product according to any previous para wherein the peptide is cyclised by joining the N- and C-termini of its main chain.
13. The product according to any previous para wherein the peptide and albumin are joined via a cross-linker.
14. The product according to para 13 wherein the cross-linker is SMCC.
15. A peptide that comprises the sequence XXNGRX" (SEQ ID NO:10), XX'DGRX" (SEQ ID NO:11) or XX'isoDGRX" (SEQ ID NO:39) wherein X is selected from the group consisting of G, C and phG; X' is selected from the group consisting of G, C and phG; and X" is selected from the group consisting of G and phG.
16. The peptide according to para 15 wherein the peptide comprises an amino acid suitable for conjugation, in addition to the NGR, DGR or isoDGR motif.
17. The peptide according to para 16 wherein the amino acid suitable for conjugation can be conjugated via its side chain.
18. The peptide according to para 17 wherein the amino acid suitable for conjugation via its side chain is selected from the group consisting of C, K and any non-standard amino acid that contains a free thiol or amine.
19. A peptide that comprises the sequence cyclic CGNGRG (SEQ ID NO:13), cyclic GCNGRG (SEQ ID NO:14), cyclic CphGNGRG (SEQ ID NO:15), cyclic CGNGRphG (SEQ ID NO:16), cyclic GCNGRphG (SEQ ID NO:17), cyclic phGCNGRG (SEQ ID NO:18), or cyclic CNGRG (SEQ ID NO:19).
20. A peptide that comprises the sequence cyclic CGDGRG (SEQ ID NO:20), cyclic GCDGRG (SEQ ID NO:21), cyclic CphGDGRG (SEQ ID NO:40), cyclic CGDGRphG (SEQ ID NO:23), cyclic GCDGRphG (SEQ ID NO:24), cyclic phGCDGRG (SEQ ID NO:41), or cyclic CDGRG (SEQ ID NO:26).
21. A peptide that comprises the sequence cyclic CGisoDGRG (SEQ ID NO:1), cyclic GCisoDGRG (SEQ ID NO:4), cyclic CphGisoDGRG (SEQ ID NO:5), cyclic CGisoDGRphG (SEQ ID NO:6), cyclic GCisoDGRphG (SEQ ID NO:7), cyclic phGCisoDGRG (SEQ ID NO:8), or cyclic CisoDGRG (SEQ ID NO:9).
22. A peptide that comprises the sequence CNGRG (SEQ ID NO:27), CDGRG (SEQ ID NO:28) or CisoDGRG (SEQ ID NO:29).
23. The peptide according to any of paras 15-22 wherein the peptide is cyclised by joining the N- and C-termini of its main chain
24. A product comprising a peptide according to any of paras 15-23 joined to an effector domain 25. The product according to para 24 wherein the peptide and effector domain are joined via a cross-linker.
26. The product according to para 25 wherein the cross-linker is SMCC.
27. The product according to any of paras 24-26 wherein the effector domain is a drug carrier, drug, drug carrier:drug complex, imaging compound, nanoparticle, nanoparticle:drug complex or nanoparticle:imaging compound complex.
28. The product according to para 27 wherein the drug carrier is a liposome or nanotube.
29. The product according to para 27 wherein the drug is an anti-cancer drug.
30. The product according to para 29 wherein the anti-cancer drug is paclitaxel.
31. The product according to para 27 wherein the drug carrier:drug complex is Abraxane.
32. The product according to para 27 wherein the imaging compound is a Qdot fluorescent nanoparticle.
33. The product according to para 27 wherein the nanoparticle is a gold nanoparticle.
34. The product according to para 27 wherein the nanoparticle:drug complex is a gold nanoparticle:tumour necrosis factor α complex.
35. A peptide that comprises a dimer of a peptide according to any of paras 15-23.
36. The dimeric peptide according to para 35 wherein the peptide is dimerised via a disulfide bond.
37. Preferably the product of the present invention inhibits tumor growth.
38. Preferably the product of the present invention inhibits angiogenisis.
39. Preferably the product of the present invention comprises a turn involving the G and R residues of the DGR motif.
40. According to another aspect of the present invention there is provided a conjugation product comprising a peptide of the present invention. Preferably the conjugation product is between a peptide of the present invention and a drug, cytokine, cytokine fragment toxin, apoptotic peptide, biological response modifier radionuclide, viral particle, gene or an imaging compound. In one embodiment the drug is an anticancer agent such as doxorubicin, melphalan, cis-platin, gemcitabine or taxol.
41. According to another aspect of the present invention there is provided a pharmaceutical composition comprising a pharmaceutically effective amount of a peptide or conjugation product of the present invention, preferably comprising a pharmaceutically acceptable carrier, diluent or excipient.
42. The composition of the present invention may be in the form of an injectable solution or suspension or a liquid for infusions.
43. The composition of the present invention may be in the form of liposomes.
44. According to another aspect of the present invention there is provided a method of treating or diagnosing a patient suffering from disorders involving αvβ3 such as but not limited to osteoporosis, arthritis, diabetic retinopathy, macular degeneration, restenosis or hemangioma comprising administering the peptide, conjugation product or pharmaceutical composition of the invention.
45. According to another aspect of the present invention there is provided a method of treating or diagnosing a patient suffering from osteoporosis, arthritis, diabetic retinopathy, macular degeneration, restenosis or hemangioma comprising administering the peptide, conjugation product or pharmaceutical composition of the invention.

46. According to another aspect of the present invention there is provided a method of treating or diagnosing a patient suffering from a cancer, such as but not limited to lung, pancreas, breast, colon, larynx or ovary cancer, comprising administering the peptide, conjugation product or pharmaceutical composition of the invention.

47. A non-limiting list of cytokines used in the conjugate of the present invention is TNFα, TNFβ, IFNα, IFNβ, IFNγ, IL-1, 2, 4, 6, 7, 12, 15, EMAP II, vascular endothelial growth factor (VEGF), PDGF, PD-ECGF or a chemokine. Preferably the cytokine of the conjugate is selected from TNF, IFNγ, IL-12 IP-10, IL-7 or EMAP II. More preferably the cytokine is selected from TNF, IFNγ, or IL-12

48. Preferably the TNF is TNFα or TNFβ.

49. In one embodiment the cytokine is derivatized with polyethylene glycol or an acyl residue.

50. In another embodiment the cytokine is further conjugated with a compound selected from the group consisting of an antibody, an antibody fragment, and biotin, wherein said antibody or fragment thereof is directed to a compound selected from the group consisting of a tumoral antigen, a tumoral angiogenic marker or a component of the extracellular matrix.

51. In another embodiment the cytokine is TNF and is conjugated to both the targeting moiety and a compound selected from the group consisting of an antibody, and antibody fragment, and biotin.

52. According to another aspect of the present invention there is provided a pharmaceutical composition comprising an effective amount of a conjugation product of TNF of the present invention, and an effective amount of IFNγ or a polynucleotide encoding therefor.

53. The composition of the present invention may further comprise another antitumor agent, such as, but not limited to doxorubicin or melphalan, or cis-platin or gemcitabine or taxol or a diagnostic tumor-imaging compound.

DETAILED DESCRIPTION

Various preferred features and embodiment of the present invention will now be described by way of non-limiting example.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Serum albumin is an abundant protein of about 67 kDa that works as a transport system for small molecules in the blood (metal ions, free fatty acids, hormones, drugs and many others) and that contributes in the maintenance of oncotic pressure [1]. Furthermore, after its degradation, this protein generates amino acids that provide nutrients to tissues [2]. This protein has a long circulating half-life (19 days) and tends to accumulate in tumors, owing to the presence of leaky capillaries and to defective lymphatic drainage [1,3]. Because of these properties and of its biocompatibility, albumin is emerging as a versatile drug carrier in a number of different applications in cancer therapy and nanomedicine [3,4]. Basically, albumin can be exploited to prolong circulating half-life and to enhance tumor uptake of low-molecular-weight drugs and peptides, or for the preparation of nanoparticles that encapsulate anti-cancer drugs, or for the preparation of labeled nanoparticles useful in the diagnostic field [3,4]. Among the various albumin-based compounds so far developed, three of them (a methotrexate-albumin conjugate, an albumin-binding pro-drug of doxorubicin and albumin-paclitaxel nanoparticles, have been clinically tested [4-9]. Notably, the albumin-paclitaxel nanoparticles (Abraxane) have been approved for the treatment of metastatic breast cancer, highlighting the importance of albumin for the successful development of new anticancer drugs. Because of the good results obtained with these drugs, many other albumin-based systems are under development in different laboratories for the delivery of a variety of therapeutic and diagnostic compounds to tumors, including chemotherapeutic drugs, cytokines, nucleic acids, photosensitizers, radionuclides, fluorescent molecules and many others [4].

The tumor homing properties of albumin-based drugs and nanoparticles could be further increased, in principle, by an "active" targeting mechanisms, e.g. by coupling albumin with ligands selective for receptors that are overexpressed in the tumor vasculature. A growing body of evidence suggest that a subset of integrins, a 24-membered family of αβ heterodimeric receptors involved in the regulation of cell adhesion, growth, survival, proliferation, migration and invasion [10-12], may represent a good target for this strategy. In particular, the αvβ3, αvβ5 and α5β1 heterodimers, which are overexpressed in tumor vessels and have a role in the regulation of angiogenesis, are an attractive target [10,11]. These integrins can recognize the Arg-Gly-Asp (RGD) sequence [13-15]. Thus, peptides containing this motif have been exploited for the preparation of new drugs and nanoparticles, including various albumin-based conjugates, capable to target the tumor neovasculature [16-18,15, 19,10,20-22]. We and other investigators have recently shown that the integrin αvβ3 can also recognize peptides containing the isoDGR motif (isoAsp-Gly-Arg), a mimetic of the RGD-integrin recognition sequence [23-26]. These peptides home in on tumor vessels, affect endothelial cell physiology and inhibit tumor growth [25,27]. Thus, peptides containing the isoDGR motif may represent good candidates for the development of ligand-tagged albumin with improved tumor vasculature-homing properties.

To have at hand an isoDGR peptide that can be coupled to albumin and to other proteins without loosing its selectivity for vascular integrins, we have designed a series of head-to-tail-cyclized isoDGR peptides and analyzed their integrin binding properties. We have identified a thiol-containing peptide that can be easily coupled to proteins and that has a good selectivity for αvβ3 and αvβ5 even after coupling to human serum albumin and to other compounds. We show that isoDGR-tagged albumin binds to endothelial cells, binds tumor vessels and inhibits tumor growth. In addition, we provide evidence to suggest that isoDGR-tagged albumin can be exploited as a new platform for the development of albumin-based drugs and nanoparticles.

The results shown below demonstrate that isoDGR-tagged albumin is an efficient tumor vasculature-homing agent endowed of anti-tumor activity. To prepare the isoDGR-tagged albumin we have synthesized new head-to-tail cyclized peptides with different molecular scaffolds having a free thiol group that enables peptide conjugation to albumin by using sulfo-SMCC, an efficient and widely used cross-linking reagent. The results of integrin binding studies showed that the peptide molecular scaffold markedly contributes to integrin recognition and selectivity. For example, c(CisoDGRGG) (SEQ ID NO:30) (isoDGR#3) could bind $\alpha v\beta 3$, $\alpha v\beta 5$, $\alpha v\beta 6$, $\alpha v\beta 8$ and $\alpha 5\beta 1$ with similar affinity, whereas c(CGisoDGRG) (SEQ ID NO:1) (isoDGR#1) was more selective for $\alpha v\beta 3$. The selectivity of isoDGR#1 for $\alpha v\beta 3$ and $\alpha v\beta 5$ was markedly improved after coupling the peptide to the linker and even more after coupling to HSA (see FIG. 10 for a schematic representation of the isoDGR#1-linker-albumin conjugate). Thus, all conjugate components isoDGR residues, peptide scaffold, linker and protein) contribute to integrin binding affinity and selectivity. The importance of the molecular scaffold and linker for peptide/integrin recognition have been documented also with other isoDGR peptides [39,23]. Considering that $\alpha v\beta 3$ and $\alpha v\beta 5$ are overexpressed by endothelial cells in tumor tissues, the isoDGR#1-linker conjugate can be exploited as a ligand for the delivery of albumin, drugs and nanoparticles to tumor vessels. This hypothesis is supported by the observation that isoDGR#1-linker-Qdot nanoparticles, a fluorescent compound, efficiently homed to tumor vessels after systemic administration to WEHI-164 tumor-bearing mice.

Remarkably, the selectivity of isoDGR#1-HSA for the $\alpha v\beta 3$ and $\alpha v\beta 5$ was superior to that of Cilengitide, a cyclic RGD-containing antagonist of these integrins, which is being tested as an anti-angiogenic/anti-tumor drug in patients [40]. For example, while the affinities of Cilengitide for $\alpha v\beta 3$ was 51 and 122-fold higher than those for $\alpha v\beta 6$ and $\alpha v\beta 8$, these ratios increased to 248 and 3028 in the case of isoDGR#1-HSA. Considering that the $\alpha v\beta 8$ is expressed in yolk sac, placenta, brain perivascular astrocytes, Schwann cells, renal glomerular mesangial cells and pulmonary epithelial cells [41-44] and that $\alpha v\beta 6$ is expressed in epithelia [45], the good selectivity of isoDGR-HSA for integrins expressed in tumor vessels might represent an important advantage.

We have previously shown that administration of disulfide-constrained isoDGR peptides to tumor bearing mice can delay tumor growth in different animal models, likely by affecting the tumor neovascularization [25,23]. The results of in vivo studies performed with isoDGR#1-HSA in fibrosarcoma- and lymphoma-bearing mice suggest that isoDGR peptides can maintain their anti-tumor activity even after conjugation to HSA over a wide range of doses (from 0.032 to 25 µg). Notably, no evidence of toxicity was obtained even with the highest dose tested. Given the emerging role of albumin as a drug carrier in a number of applications, the good selectivity of isoDGR-tagged albumin for tumor vessels and its inherent anticancer activity suggest that this conjugate may represent a valid tool for the generation of more selective and more potent nanomedicines. This hypothesis is supported by the observation that isoDGR#1-HSA maintains its ability to recognize $\alpha v\beta 3$ even after adsorption on colloidal gold, a nanoparticles-based platform used for the preparation of anticancer [35]. Furthermore, tagging Abraxane (an albumin based anticancer drug) with isoDGR#1 improved its cytotoxic activity against $\alpha v\beta 3$-positive endothelial cells, but not against $\alpha v\beta 3$-negative keratinocytes.

In conclusion, the results show that isoDGR#1-tagged albumin is a selective ligand of $\alpha v\beta 3$ and $\alpha v\beta 5$ and an efficient vascular targeting agent endowed of anti-tumor activity. This product could be exploited as a versatile tool for the preparation of drugs and nanoparticles with improved tumor vasculature-homing properties.

The present invention relates to peptides that comprise a motif selected from a group consisting of NGR, DGR and isoDGR. The NGR, DGR and isoDGR motifs enable the peptide to be targeted to cells expressing receptors that NGR, DGR and isoDGR motifs bind to. The peptides of the present invention may be joined to an effector domain. The effector domain assists use of the peptides of the invention in various applications such as medical treatment, diagnosis and laboratory assays. For example, the tumour horning properties of isoDGR peptides may be used to provide peptides for tumour therapy or diagnosis. A non-limiting list of effector domains includes an effector domain that is a drug carrier, drug, drug carrier:drug complex, imaging compound, nanoparticle, nanoparticle:drug complex, nanoparticle:imaging compound complex, avidin, neutravidin or streptavidin. Peptides of the present invention may be joined to albumin as well as an additional effector domain.

Nanoparticle:drug complexes may comprise one or more drugs. A non-limiting list of drugs includes drugs selected from a cytokine, antigen, antibody, an anti-cancer drug, or a combination thereof. The cytokine may be TNF, IL-12, IFNgamma or EMAP-II. The antigen may be a tumor antigen. The drug may be an immunomodulatory drug. The immunomodulatory drug may be IL-10.

Peptides joined to albumin may be joined to nanoparticle or nanoparticle:drug complexes. The nanoparticles may be gold nanoparticles.

Peptides of the present invention may be joined to albumin and to nanoparticle:drug complexes comprising one or more drugs. The nanoparticle:drug complexes may comprise one or more cytokines together with a biological response modifier to a tumor microenvironment. A non-limiting list of biological response modifiers to a tumor microenvironment includes a lipopolysaccharide or other agents capable of inducing TNF and other anticancer cytokines. The nanoparticle:drug complexes may also comprise at least one antigen capable of eliciting a specific immune response against tumors.

DGR, NGR Motif

It is well known that aspartic acid may exist in a different structural isomeric form, namely isoaspartic acid.

Aspartic acid and isoaspartic acid are each chiral molecules, and the different isomers can be referred to as $_L$-Asp ($_LD$), $_L$isoAsp ($_L$isoD), $_D$Asp ($_DD$) and $_D$isoAsp ($_D$isoD) where $_L$isoD and $_D$isoD represent the entantiomers of isoaspartic acid and $_LD$ and $_DD$ represent the enantiomers of aspartic acid.

When the prior art refers to DGR, it in essence refers to $_L$DGR. As used herein, the term DGR refers to a DGR motif that comprises $_DD$ and/or $_L$isoD or mixtures thereof and which may further comprise $_LD$ and $_D$isoD. Preferably, the DGR is generated by deamidation of the corresponding NGR motif. In one embodiment the DGR motif comprises at least 10 w/w % $_L$isoDGR. In another embodiment the DGR motif comprises at least 10 w/w % $_D$DGR By a peptide or targeting moiety comprising an isoDGR motif it is meant a peptide or targeting moiety wherein the DGR motif is substantially in the form of isoDGR. By substantially, it is meant the w/w % of peptide or targeting moiety comprising the isoDGR motif relative to total DGR containing peptide or targeting moiety is greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%. The isoDGR may comprise both enantiomers of $_{L/D}$isoD, but preferably comprises at least 5, more preferably at least 10, more preferably at least 30, more preferably at least 40, more preferably at least 50 w/w % of $_L$isoD.

By a peptide or targeting moiety comprising an $_L$isoDGR motif it is meant a peptide or targeting moiety wherein the DGR motif is substantially in the form of $_L$isoDGR. By substantially it is meant the w/w % of peptide or targeting moiety comprising the $_L$isoDGR motif relative to total DGR containing peptide or targeting moiety is greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

By a peptide or targeting moiety comprising a $_D$DGR motif it is meant a peptide or targeting moiety wherein the DGR motif is substantially in the form of $_D$DGR. By substantially it is meant the w/w % of peptide or targeting moiety comprising the $_D$DGR motif relative to total DGR containing peptide or targeting moiety is greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

The DGR motif of the present invention preferably comprises a turn involving the G and R residues. When the DGR motif is arrived at by deamidation of the corresponding NGR motif, it is preferable that the NGR motif comprises a turn involving the G and R residues. The structure-activity relationship of linear and cyclic peptides containing the NGR motif and their ability to target tumors is discussed in Colombo et al., J. Biol. Chem., 2002, 49, 47891-47897. The Experiments carried out in animal models showed that both GNGRG (SEQ ID NO:31) and CNGRC (SEQ ID NO:32) can target TNF to tumors. Molecular dynamic simulation of cyclic CNGRC (SEQ ID NO:32) showed the presence of a bend geometry involving residues Gly$^3$-Arg$^4$, stabilised by the formation of a disulphide bridge. Molecular dynamic simulation of the same peptide without disulfide constraints showed that the most populated and thermodynamically favoured configuration is characterised by the presence of a β-turn involving residues Gly$^3$-Arg$^4$. These results suggest that the NGR motif has a strong propensity to form a β-turn in linear peptides and may explain the finding that GNGRG (SEQ ID NO:31) peptide can target TNF to tumors, albeit to a lower extent than CNGRC (SEQ ID NO:32). Further information about NGR-containing peptides can be found in WO2004/105782.

Peptide

The term "peptide" as used herein includes polypeptides and proteins. The term "polypeptide" includes single-chain polypeptide molecules as well as multiple-polypeptide complexes where individual constituent polypeptides are linked by covalent or non-covalent means.

Peptides of the present invention may be administered therapeutically to patients. It is preferred to use peptides that do not consisting solely of naturally-occurring amino acids but which have been modified, for example to reduce immunogenicity, to increase circulatory half-life in the body of the patient, to enhance bioavailability and/or to enhance efficacy and/or specificity.

Peptide Variants, Derivatives and Fragments

The terms "variant" or "derivative" in relation to the amino acid sequences of the present invention includes any substitution of, variation of, modification of, replacement of, deletion of or addition of one (or more) amino acids from or to the sequence providing the resultant amino acid sequence preferably has targeting activity, preferably having at least 25 to 50% of the activity as the polypeptides presented in the sequence listings, more preferably at least substantially the same activity.

Thus, sequences may be modified for use in the present invention. Typically, modifications are made that maintain the activity of the sequence. Thus, in one embodiment, amino acid substitutions may be made, for example from 1, 2 or 3 to 10, 20 or 30 substitutions provided that the modified sequence retains at least about 25 to 50% of, or substantially the same activity. However, in an alternative embodiment, modifications to the amino acid sequences of a polypeptide of the invention may be made intentionally to reduce the biological activity of the polypeptide. For example truncated polypeptides that remain capable of binding to target molecule but lack functional effector domains may be useful.

In general, preferably less than 20%, 10% or 5% of the amino acid residues of a variant or derivative are altered as compared with the corresponding region depicted in the sequence listings.

Amino acid substitutions may include the use of non-naturally occurring analogues, for example to increase blood plasma half-life of a therapeutically administered polypeptide (see below for further details on the production of peptide derivatives for use in therapy).

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

Polypeptides of the invention also include fragments of the above mentioned polypeptides and variants thereof, including fragments of the sequences. Preferred fragments include those which include an epitope or binding domain. Suitable fragments will be at least about 5, e.g. 10, 12, 15 or 20 amino acids in length. They may also be less than 200, 100 or 50 amino acids in length. Polypeptide fragments of the proteins and allelic and species variants thereof may contain one or more (e.g. 2, 3, 5, or 10) substitutions, deletions or insertions, including conserved substitutions. Where substitutions, deletion and/or insertions have been made, for example by means of recombinant technology, preferably less than 20%, 10% or 5% of the amino acid residues depicted in the sequence listings are altered.

Polypeptides and conjugates of the invention are typically made by recombinant means, for example as described below. However they may also be made by synthetic means using techniques well known to skilled persons such as solid phase synthesis. Various techniques for chemical synthesising peptides are reviewed by Borgia and Fields, 2000, TibTech 18: 243-251 and described in detail in the references contained therein.

Polynucleotides

Polynucleotides for use in the invention comprise nucleic acid sequences encoding peptides and conjugates of the invention. In particular, the polynucleotides may encode precursor peptides or conjugates comprising the NGR motif which, upon deamidation, renders peptides and conjugates. comprising the corresponding DGR motif.

It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the field of the invention.

Such modifications may be carried out in order to enhance the in vivo activity or life span of polynucleotides.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as E. coli, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific promoters specific for certain cells may also be used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Vectors and polynucleotides of the invention may be introduced into host cells for the purpose of replicating the vectors/polynucleotides and/or expressing the proteins of the invention encoded by the polynucleotides of the invention. Although the proteins of the invention may be produced using prokaryotic cells as host cells, it is preferred to use eukaryotic cells, for example yeast, insect or mammalian cells, in particular mammalian cells.

Vectors/polynucleotides of the invention may introduced into suitable host cells using a variety of techniques known in the art, such as transfection, transformation and electroporation. Where vectors/polynucleotides of the invention are to be administered to animals, several techniques are known in the art, for example infection with recombinant viral vectors such as retroviruses, herpes simplex viruses and adenoviruses, direct injection of nucleic acids and biolistic transformation.

Host cells comprising polynucleotides of the invention may be used to express conjugates of the invention. Host cells may be cultured under suitable conditions which allow expression of the polypeptides and conjugates of the invention. Expression of the products of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Conjugates

The present invention also relates to a conjugate which is a molecule comprising a peptide or targeting moiety of the invention linked to at least one other agent, including, but not limited to, a drug, a cytokine, a toxin, an apoptotic peptide, a radionuclide, a viral particle, a gene or an imaging compound, formed through genetic fusion or chemical coupling. A non-limiting list of cytokines used in the conjugate of the present invention is TNFα, TNFβ, IFNα, IFNβ, IFNγ, IL-1, 2, 4, 6, 7, 12, 15, EMAP II, vascular endothelial growth factor (VEGF), PDGF, PD-ECGF or a chemokine.

Conjugates include fusion proteins in which the peptide or targeting moiety is linked to an agent via its polypeptide backbone through genetic expression of a DNA molecule encoding these proteins, directly synthesised proteins and coupled proteins in which pre-formed sequences are associated by a cross-linking agent. The term is also used herein to include associations, such as aggregates.

According to a preferred embodiment, there is provided a conjugation product between TNF and the peptide of the present invention.

The pharmacokinetic of the modified cytokines according to the invention can be improved by preparing polyethylene glycol derivatives, which allow to extend the plasmatic half-life of the cytokines themselves.

Cytokines

Drug penetration into neoplastic cells is critical for the effectiveness of solid-tumor chemotherapy. To reach cancer cells in solid tumors, chemotherapeutic drugs must enter the drug blood vessels, cross the vessel wall and finally migrate through the interstitium. Heterogeneous tumor perfusion, vascular permeability and cell density, and increased interstitial pressure may represent critical barriers that may limit the penetration of drugs into neoplastic cells and, consequently, the effectiveness of chemotherapy. Cytokines which have the effect of affecting these factors are therefore useful in the present invention. A non-limiting list of cytokines which may be used in the present invention is: TNFα, TNFβ, IFNα, IFNβ, IFNγ, IL-1, 2, 4, 6, 7, 12, 15, IP-10, EMAP II, vascular endothelial growth factor (VEGF), PDGF, PD-ECGF or a chemokine.

TNF

TNF acts as an inflammatory cytokine and has the effect of inducing alteration of the endothelial barrier function, reducing of tumor interstitial pressure, and increasing chemotherapeutic drug penetration and tumor vessel damage.

The first suggestion that a tumor necrotizing molecule existed was made when it was observed that cancer patients occasionally showed spontaneous regression of their tumors following bacterial infections. Subsequent studies in the 1960s indicated that host-associated (or endogenous) mediators, manufactured in response to bacterial products, were likely responsible for the observed effects. In 1975 it was shown that a bacterially-induced circulating factor had strong anti-tumor activity against tumors implanted in the skin in mice. This factor, designated tumor necrosis factor (TNF), was subsequently isolated, cloned, and found to be the prototype of a family of molecules that are involved with immune regulation and inflammation. The receptors for TNF and the other members of the TNF superfamily also constitute a superfamily of related proteins.

TNF-related ligands usually share a number of common features. These features do not include a high degree of overall amino acid (aa) sequence homology. With the exception of nerve growth factor (NGF) and TNF-beta, all ligands are synthesised as type II transmembrane proteins (extracellular C-terminus) that contain a short cytoplasmic segment (10-80 aa residues) and a relatively long extracellular region (140-215 aa residues). NGF, which is structurally unrelated to TNF, is included in this superfamily only because of its ability to bind to the TNFRSF low affinity NGF receptor (LNGFR). NGF has a classic signal sequence peptide and is secreted. TNF-β, in contrast, although also fully secreted, has a primary structure much more related to type II transmembrane proteins. TNF-β might be considered as a type II protein with a non-functional, or inefficient, transmembrane segment. In general, TNFSF members form trimeric structures, and their monomers are composed of beta-strands that orient themselves into a two sheet structure. As a consequence of the trimeric structure of these molecules, it is suggested that the ligands and receptors of the TNSF and TNFRSF superfamilies undergo "clustering" during signal transduction.

TNF-α: Human TNF-α is a 233 aa residue, nonglycosylated polypeptide that exists as either a transmembrane or soluble protein. When expressed as a 26 kDa membrane bound protein, TNF-α consists of a 29 aa residue cytoplasmic domain, a 28 aa residue transmembrane segment, and a 176 aa residue extracellular region. The soluble protein is created by a proteolytic cleavage event via an 85 kDa TNF-alpha converting enzyme (TACE), which generates a 17 kDa, 157 aa residue molecule that normally circulates as a homotrimer.

TNF-β/LT-α: TNF-β, otherwise known as lymphotoxin-α (LT-α) is a molecule whose cloning was contemporary with that of TNF-α. Although TNF-β circulates as a 171 aa residue, 25 kDa glycosylated polypeptide, a larger form has been found that is 194 aa residues long. The human TNF-β cDNA codes for an open reading frame of 205 aa residues (202 in the mouse), and presumably some type of proteolytic processing occurs during secretion. As with TNF-α, circulating TNF-β exists as a non-covalently linked trimer and is known to bind to the same receptors as TNF-α.

In one embodiment the TNF is a mutant form of TNF capable of selectively binding to one of the TNF receptors (Loetscher H et al (1993) J Biol Chem 268:26350-7; Van Ostade X et al (1993) Nature 361:266-9).

The maximum tolerated dose of bolus TNF in humans is 218-410 μg/m² (Fraker et al., 1995) about 10-fold lower than the effective dose in animals. Based on data from murine models it is believed that an at least 10 times higher dose is necessary to achieve anti-tumor effects in humans (Schraffordt Koops et al., 1998). In the first clinical study on hyperthermic isolated-limb perfusion, high response rates were obtained with the unique dose of 4 mg of TNF in combination with melphalan and interferon γ (Lienard et al., 1992). Other works showed that interferon γ can be omitted and that even lower doses of TNF can be sufficient to induce a therapeutic response (Hill et al., 1993; Eggermont et al., 1996). As the two cytokines exert synergistic effects on endothelial cells, their combined, selective targeting thereon is likely to result in stronger anti-tumor activity thus allowing to overcome the problems of systemic toxicity usually encountered in cancer therapy with the same cytokines used in combination. Furthermore, it is known that TNF can decrease the barrier function of the endothelial lining vessels, thus increasing their permeability to macromolecules. Taking advantage of the lower toxicity of treatment with the modified TNF molecules according to the invention, and of their tumor vessels homing properties, an alternative application is their use to increase the permeability of tumor vessels to other compounds, either for therapeutic or diagnostic purposes. For instance the modified TNF can be used to increase the tumor uptake of radiolabelled antibodies or hormones (tumor-imaging compounds) in radioimmunoscintigraphy or radioimmunotherapy of tumors. Alternatively, the uptake of chemotherapeutic drugs, immunotoxins, liposomes carrying drugs or genes, or other anticancer drugs could also be increased, so that their antitumor effects are enhanced.

Many other inflammatory cytokines also have the property of increasing endothelial vessel permeability, and it will be appreciated that the invention can be applied to such cytokines, together with agents which increase expression of such cytokines. Inflammatory cytokines, also known as pro-inflammatory cytokines, are a number of polypeptides and glycoproteins with molecular weights between 5 kDa and 70 kDa. They have a stimulating effect on the inflammatory response. The most important inflammatory cytokines are TNF, IL-1, IL-6 and IL-8.

A Table of some cytokines classified as inflammatory cytokines is shown below:

| Inflammatory Cytokines | |
|---|---|
| Group | Individual cytokines |
| Endogenous cytokines | IL-1, TNF-α, IL-6 |
| Up-regulation | IL-1, TNF-α, IL-6, IFN-α, INF-β, chemokines |
| Stimulation of the production of acute phase reactants | IL-1, IL-6, IL-11, TNF-α, INF-γ, TGF-β, LIF, OSM, CNTF |
| Chemoattractant cytokines | |
| CXC chemokines | IL-8, PF-4, PBP, NAP-2, β-TG |
| CC chemokines | MTP-1α, MIP-1β, MCP-1, MCP-2, MCP-3, RANTES |
| C chemokines | Lymphotactin |
| Stimulation of inflammatory cytokines | IL-12 |

TGF-β: transforming growth factor, LIF: leukemia inhibitory factor; OSM: oncostatin M; CNTF: ciliary neurotrophic factor; PF-4: platelet factor 4; PBP: platelet basic protein; NAP-2: neutrophil activating protein 2; β-TG: β-thromboglobulin; MIP: macrophage inflammatory protein; MCP: monocyte chemoattractant protein.

The up-regulation of inflammatory response is also performed by IL-11, IFN-α, ITN-β, and especially by the members of the chemokine superfamily. TGF-β in some situations has a number of inflammatory activities including chemoattractant effects on neutrophils, T lymphocytes and inactivated monocytes.

IFN-γ

A large body of evidence suggests that interferon-γ (IFNγ), a pleiotropic cytokine mainly produced by T-lymphocytes and natural killer cells (Farrar, et al., 1993; Boehm et al., 1997) can promote anti-tumor responses (Curnis et al., 2005). For instance, IFNγ can induce anti-proliferative and proapoptotic effects on many tumor cell types, can inhibit tumor angiogenesis and activate natural killer cells and macrophages to kill a variety of tumor cell targets. IFNγ is also an important regulator of $CD4^+$ T helper cells, is the major physiological macrophage-activating factor and can augment the expression of MHC-I and II on cancer and endothelial cells. Within tumor stroma IFNγ can induce cytokine and chemokine secretion, including IP-10 (IFN-inducible Protein 10), an angiostatic protein and a chemoattractant factor for lymphocytes and monocytes. Evidence has been obtained to suggest that IFNγ produced by tumor-infiltrating macrophages plays a role in tumor blood vessel destruction. Combined treatment of endothelial cells with IFNγ and tumor necrosis factor-α (TNF) results in synergistic cytotoxic effects, likely important for tumor vasculature destruction. IFNγ can also increase the production of TNF by activated macrophages, as well as the expression of TNF-receptors in various cell types. As a consequence of these effects on tumor vasculature and on cells of the immune system IFNγ can activate inflammatory/immune responses against established tumors and inhibit tumor growth.

IFNγ exists as a homodimer of two noncovalently bound polypeptide subunits. The primary sequence of wildtype human IFNγ (huIFNG) was reported by Gray et al., 1982; Taya et al., 1982; Devos et al., 1982; and Rinderknecht et al., 1984, and in EP 77670, EP 89676 and EP 110044. The 3D structure of huIFNG was reported by Ealick et al., 1991.

IL-12

Interleukin 12 (IL-12), also referred to as natural killer cell stimulatory factor ("NKSF") or cytotoxic lymphocyte maturation factor ("CLMF"), is a potent immunoregulatory molecule that plays a role in a wide range of diseases. Human IL-12 has been characterized as a cytokine with a unique structure and pleiotropic effects (Kobayashi, et al., 1989; Seder, et al., 1993; Ling, et al., 1995; Podlaski, et al., 1992). IL-12 plays a critical role in the pathology associated with several diseases involving immune and inflammatory responses. A review of IL-12, its biological activities, and its role in disease can be found in Gately et al., 1998. An important role of IL-12 in vivo is its ability to induce IFNγ production by both natural killer (NK) and T cells.

Structurally, IL-12 is a heterodimeric protein comprising a 35 kDa subunit (p35) and a 40 kDa subunit (p40) which are both linked together by a disulfide bridge (referred to as the "p70 subunit"). The heterodimeric protein is produced primarily by antigen-presenting cells such as monocytes, macrophages and dendritic cells. These cell types also secrete an excess of the p40 subunit relative to p70 subunit.

IL-2

Because of the central role of the IL-2/IL-2R system in mediation of the immune and inflammatory responses, it is obvious that monitoring and manipulation of this system has important diagnostic and therapeutic implications. IL-2 has shown promise as an anti-cancer drug by virtue of its ability to stimulate the proliferation and activities of tumor-attacking LAK and TIL (tumor-infiltrating lymphocytes) cells. However, problems with IL-2 toxicity are still of concern and merit investigation. The present invention addresses this problem.

IL-15

Interleukin 15 (IL-15) is a novel cytokine that shares many biological properties with, but lacks amino acid sequence homology to, IL-2. IL-15 was originally identified in media conditioned by a monkey kidney epithelial cell line (CVI/EBNA) based on its mitogenic activity on the murine T cell line, CTLL-2. IL-15 was also independently discovered as a cytokine produced by a human adult T cell leukemia cell line (HuT-102) that stimulated T cell proliferation and was designated IL-T. By virtue of its activity as a stimulator of T cells, NK cells, LAK cells, and TILs, IL-2 is currently in clinical trials testing its potential use in treatments for cancer and for viral infections. Because of its similar biological activities, IL-15 should have similar therapeutic potential.

Chemokines

Chemokines are a superfamily of mostly small, secreted proteins that function in leukocyte trafficking, recruiting, and recirculation. They also play a critical role in many pathophysiological processes such as allergic responses, infectious and autoimmune diseases, angiogenesis, inflammation, tumor growth, and hematopoietic development. Approximately 80 percent of these proteins have from 66 to 78 amino acids (aa) in their mature form. The remainder are larger with additional aa occurring upstream of the protein core or as part of an extended C-terminal segment. All chemokines signal through seven transmembrane domain G-protein coupled receptors. There are at least seventeen known chemokine receptors, and many of these receptors exhibit promiscuous binding properties whereby several different chemokines can signal through the same receptor.

Chemokines are divided into subfamilies based on conserved aa sequence motifs. Most family members have at least four conserved cysteine residues that form two intramolecular disulfide bonds. The subfamilies are defined by the position of the first two cysteine residues:

The alpha subfamily, also called the CXC chemokines, have one aa separating the first two cysteine residues. This group can be further subdivided based on the presence or absence of a glu-leu-arg (ELR) aa motif immediately preceding the first cysteine residue. There are currently five CXC-specific receptors and they are designated CXCR1 to CXCR5. The $ELR^+$ chemokines bind to CXCR2 and generally act as neutrophil chemoattractants and activators. The ELR-chemokines bind CXCR3 to -5 and act primarily on lymphocytes. At the time of this writing, 14 different human genes encoding CXC chemokines have been reported in the scientific literature with some additional diversity contributed by alternative splicing.

In the beta subfamily, also called the CC chemokines, the first two cysteines are adjacent to one another with no intervening aa. There are currently 24 distinct human beta subfamily members. The receptors for this group are designated CCR1 to CCR11. Target cells for different CC family members include most types of leukocytes.

There are two known proteins with chemokine homology that fall outside of the alpha and beta subfamilies. Lymphotactin is the lone member of the gamma class (C chemokine) which has lost the first and third cysteines. The lymphotactin receptor is designated XCR1. Fractalkine, the only known member of the delta class ($CX_3C$ chemokine), has three intervening aa between the first two cysteine residues. This molecule is unique among chemokines in that it is a transmembrane protein with the N-terminal chemokine domain fused to a long mucin-like stalk. The fractalkine receptor is known as $CX_3CR1$.

VEGF

The present invention is also applicable to Vasculature Endothelial Growth Factor (VEGF). Angiogenesis is a process of new blood vessel development from pre-existing vasculature. It plays an essential role in embryonic development, normal growth of tissues, wound healing, the female reproductive cycle (i.e., ovulation, menstruation and placental development), as well as a major role in many diseases. Particular interest has focused on cancer, since tumors cannot grow beyond a few millimeters in size without developing a new blood supply. Angiogenesis is also necessary for the spread and growth of tumor cell metastases.

One of the most important growth and survival factors for endothelium is VEGF. VEGF induces angiogenesis and endothelial cell proliferation and it plays an important role in regulating vasculogenesis. VEGF is a heparin-binding glycoprotein that is secreted as a homodimer of 45 kDa. Most types of cells, but usually not endothelial cells themselves, secrete VEGF. Since the initially discovered VEGF, VEGF-A, increases vascular permeability, it was known as vascular permeability factor. In addition, VEGF causes vasodilatation, partly through stimulation of nitric oxide synthase in endothelial cells. VEGF can also stimulate cell migration and inhibit apoptosis. There are several splice variants of VEGF-A. The major ones include: 121, 165, 189 and 206 amino acids (aa), each one comprising a specific exon addition.

EMAP II

Endothelial-Monocyte Activating Polypeptide-II (EMAP-II) is a cytokine that is an antiangiogenic factor in tumor vascular development, and strongly inhibits tumor growth. Recombinant human EMAP-II is an 18.3 kDa protein containing 166 amino acid residues. EMAP II has also been found to increase endothelial vessel permeability.

PDGF

It has also been proposed that platelet-derived growth factor (PDGF) antagonists might increase drug-uptake and therapeutic effects of a broad range of anti-tumor agents in common solid tumors. PDGF is a cytokine of 30 kDA and is released by platelets on wounding and stimulates nearby cells to grow and repair the wound.

PD-ECGF

As its name suggests, platelet-derived endothelial cell growth factor (PD-ECGF) was originally isolated from platelets based on its ability to induce mitosis in endothelial cells. Its related protein is gliostatin.

Antibodies

As used herein, an "antibody" refers to a protein consisting of one or more polypeptides substantially encoded by immunoglobulin genes or fragments of immunoglobulin genes. Antibodies may exist as intact immunoglobulins or as a number of fragments, including those well-characterised fragments produced by digestion with various peptidases. While various antibody fragments are defined in terms of the digestion of an intact antibody, one of skill will appreciate that antibody fragments may be synthesised de novo either chemically or by utilising recombinant DNA methodology. Thus, the term antibody, as used herein also includes antibody fragments either produced by the modification of whole antibodies or synthesised de novo using recombinant DNA methodologies. Antibody fragments encompassed by the use of the term "antibodies" include, but are not limited to, Fab, Fab', F (ab') 2, scFv, Fv, dsFv diabody, and Fd fragments.

The invention also provides monoclonal or polyclonal antibodies to the surface proteins. Thus, the present invention further provides a process for the production of monoclonal or polyclonal antibodies to polypeptides of the invention.

If polyclonal antibodies are desired, a selected mammal (e.g., mouse, rabbit, goat, horse, etc.) is immunised with an immunogenic polypeptide bearing an epitope(s). Serum from the immunised animal is collected and treated according to known procedures. If serum containing polyclonal antibodies to an epitope contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against binding cell surface epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. As mentioned above such fragments include Fv, F(ab') and F(ab')$_2$ fragments, as well as single chain antibodies (scFv). Furthermore, the antibodies and fragments thereof may be humanised antibodies, for example as described in EP-A-239400.

Agent

As used herein, the term "agent" includes, but is not limited to, a compound, such as a test compound, which may be obtainable from or produced by any suitable source, whether natural or not. The agent may be designed or obtained from a library of compounds which may comprise peptides, as well as other compounds, such as small organic molecules and particularly new lead compounds. By way of example, the agent may be a natural substance, a biological macromolecule, or an extract made from biological materials such as bacteria, fungi, or animal (particularly mammalian) cells or tissues, an organic or an inorganic molecule, a synthetic test compound, a semi-synthetic test compound, a structural or functional mimetic, a peptide, a peptidomimetics, a derivatised test compound, a peptide cleaved from a whole protein, or a peptides synthesised synthetically (such as, by way of example, either using a peptide synthesizer) or by recombinant techniques or combinations thereof, a recombinant test compound, a natural or a non-natural test compound, a fusion protein or equivalent thereof and mutants, derivatives or combinations thereof.

The agent can be an amino acid sequence or a chemical derivative thereof. The substance may even be an organic compound or other chemical. The agent may even be a nucleotide sequence—which may be a sense sequence or an anti-sense sequence.

Pharmaceutical Formulations

The present invention also provides a pharmaceutical composition for treating an individual wherein the composition comprises a therapeutically effective amount of a peptide, polynucleotide, conjugate and drug combinations of the present invention.

A composition of the present invention comprising a peptide or conjugate comprising an isoDGR motif is substantially free of peptides or conjugates comprising other forms of DGR. By substantially free, it is meant the w/w % of isoDGR containing peptide or conjugate (i.e., peptide or conjugate wherein the DGR motif is all in the isoDGR form) present in the composition relative to total DGR containing peptide or conjugate (i.e. in all isomeric forms) present in the composition is greater than 50%, more preferably greater than 55% more preferably greater than 60%, more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

A composition of the present invention comprising a peptide or conjugate comprising an $_L$isoDGR motif is substantially free of peptides or conjugates comprising other forms of DGR. By substantially free, it is meant the w/w % of the $_L$isoDGR containing peptide or conjugate (i.e., peptide or conjugate wherein the DGR motif is all in the $_L$isoDGR form) present in the composition relative to total DGR containing peptide or conjugate (i.e. in all isomeric forms) present in the composition is greater than 50%, more preferably greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

A composition of the present invention comprising a peptide or conjugate comprising a $_D$DGR motif is substantially free of peptides or conjugates comprising other forms of DGR. By substantially free, it is meant the w/w % of the $_D$DGR containing peptide or conjugate (i.e., peptide or conjugate wherein the DGR motif is all in the $_D$DGR form) present in the composition relative to total DGR containing peptide or conjugate (i.e. in all isomeric forms) present in the composition is greater than 50%, more preferably greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system). Suitable carriers and diluents include isotonic saline solutions, for example phosphate-buffered saline. Details of excipients may be found in The Handbook of Pharmaceutical Excipients, 2nd Edn, Eds Wade & Weller, American Pharmaceutical Association.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Formulations for oral or parenteral administration are preferred. Formulations for parenteral administration comprise injectable solutions or suspensions and liquids for infusions. For the preparation of the parenteral forms, an effective amount of the active ingredient will be dissolved or suspended in a sterile carrier, optionally adding excipients such as solubilizers, isotonicity agents, preservatives, stabilizers, emulsifiers or dispersing agents, and it will be subsequently distributed in sealed vials or ampoules.

The composition may be formulated such that administration daily, weekly or monthly will provide the desired daily dosage. It will be appreciated that the composition may be conveniently formulated for administrated less frequently, such as every 2, 4, 6, 8, 10 or 12 hours.

Polynucleotides/vectors encoding polypeptide components may be administered directly as a naked nucleic acid construct, preferably further comprising flanking sequences homologous to the host cell genome.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosage regimens described are intended only as a guide since a skilled practitioner will be able to determine readily the optimum route of administration and dosage regimens for any particular patient and condition.

The preparation of peptides, and in particular cytokines, in form of liposomes can improve the biological activity thereof. It has, in fact, been observed that acylation of the TNF amino groups induces an increase in its hydrophobicity without loss of biological activity in vitro. Furthermore, it has been reported that TNF bound to lipids has unaffected cytotoxicity in vitro, immunomodulating effects and reduced toxicity in vivo (Deb et al., 1989, 1990).

Preferably compositions of the present invention comprising peptides and conjugates which contain DGR motifs according to the present invention are substantially free of the corresponding peptides and conjugates which contain the corresponding NGR motif. Preferably the proportion of DGR containing peptide relative to the total peptide (i.e., DGR and NGR containing peptide) is more than 60%, more preferably 70%, more preferably 80%, more preferably 85%, more preferably 90%, more preferably 95%, more preferably 97%, more preferably 99% w/w.

Treatment

The peptides, conjugates and compositions of the invention may be used in therapeutic treatment.

It is to be appreciated that all references herein to treatment include curative, palliative and prophylactic treatment.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species.

In one embodiment the peptides, conjugates or pharmaceutical compositions may be used to treat or prevent cancer including but not limited to cancer of the lung, pancreas, breast, colon, larynx or ovary. Preferably the cancer comprises a solid tumor.

In another embodiment, the peptides and/or conjugates may be used to treat or prevent diseases involving angiogenisis, such as diseases associated with $\alpha v \beta 3$ expression.

Angiogenesis is a process of tissue vascularization that involves the growth of new developing blood vessels into a tissue, and is also referred to as neo-vascularization. The process is mediated by the infiltration of endothelial cells and smooth muscle cells. The process is believed to proceed in any one of three ways: the vessels can sprout from pre-existing vessels, de-novo development of vessels can arise from precursor cells (vasculogenesis), or existing small vessels can enlarge in diameter (Blood et al., 1990).

There are a variety of diseases in which angiogenesis is believed to be important, referred to as angiogenic diseases, including but not limited to, inflammatory disorders such as immune and non-immune inflammation, arthritis, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like which require neovascularization to support tumor growth.

Thus, methods which inhibit angiogenesis in a diseased tissue ameliorates symptoms of the disease and, depending upon the disease, can contribute to cure of the disease.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues. Exemplary tumor tissue angiogenesis, and inhibition thereof, is described in the Examples.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods can also apply to inhibition of tumor tissue growth, to inhibition of tumor metastases formation, and to regression of established tumors.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition of restenosis by inhibiting angiogenesis according to the present methods in a patient following angioplasty procedures.

The peptides, conjugates and pharmaceutical compositions of the invention can be used in combined, separated or sequential preparations, also with other diagnostic or therapeutic substances.

In one embodiment of this aspect of the present invention, a conjugate of the present invention may be administered at a dose of from in the range of 0.5 to 500 ng/kg, preferably in the range of 1 to 50 ng/kg, more preferably in the range of 5 to 15 ng/kg.

The routes of administration and dosage regimens described are intended only as a guide since a skilled practitioner will be able to determine readily the optimum route of administration and dosage regimens for any particular patient and condition.

DESCRIPTION OF THE FIGURES

Figures

Aminoacids are represented with the single letter code; isoD, isoaspartate; phG, D-phenylglycine; ac, acetyl; S—S, disulfide bridge; SH, free thiol group. Peptide sequences and code numbers are reported below each structure (c, head-to-tail cyclization).

Figure 2:
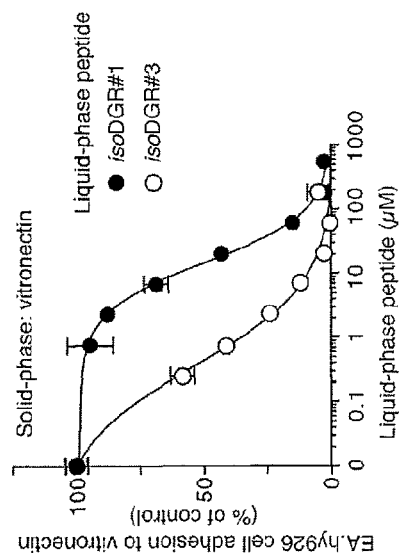

FIG. 2. Head-to-tail cyclized isoDGR peptides inhibit endothelial cell adhesion to vitronectin.

Endothelial cell (EA.hy926) adhesion to microtiter plates coated with human vitronectin was carried out as described ([25]). IsoDGR#1 and isoDGR#3 were added to the supernatant during cell adhesion. Data from a representative experiment of three independent experiments is shown. Mean±S.E (n=3).

Figure 3:
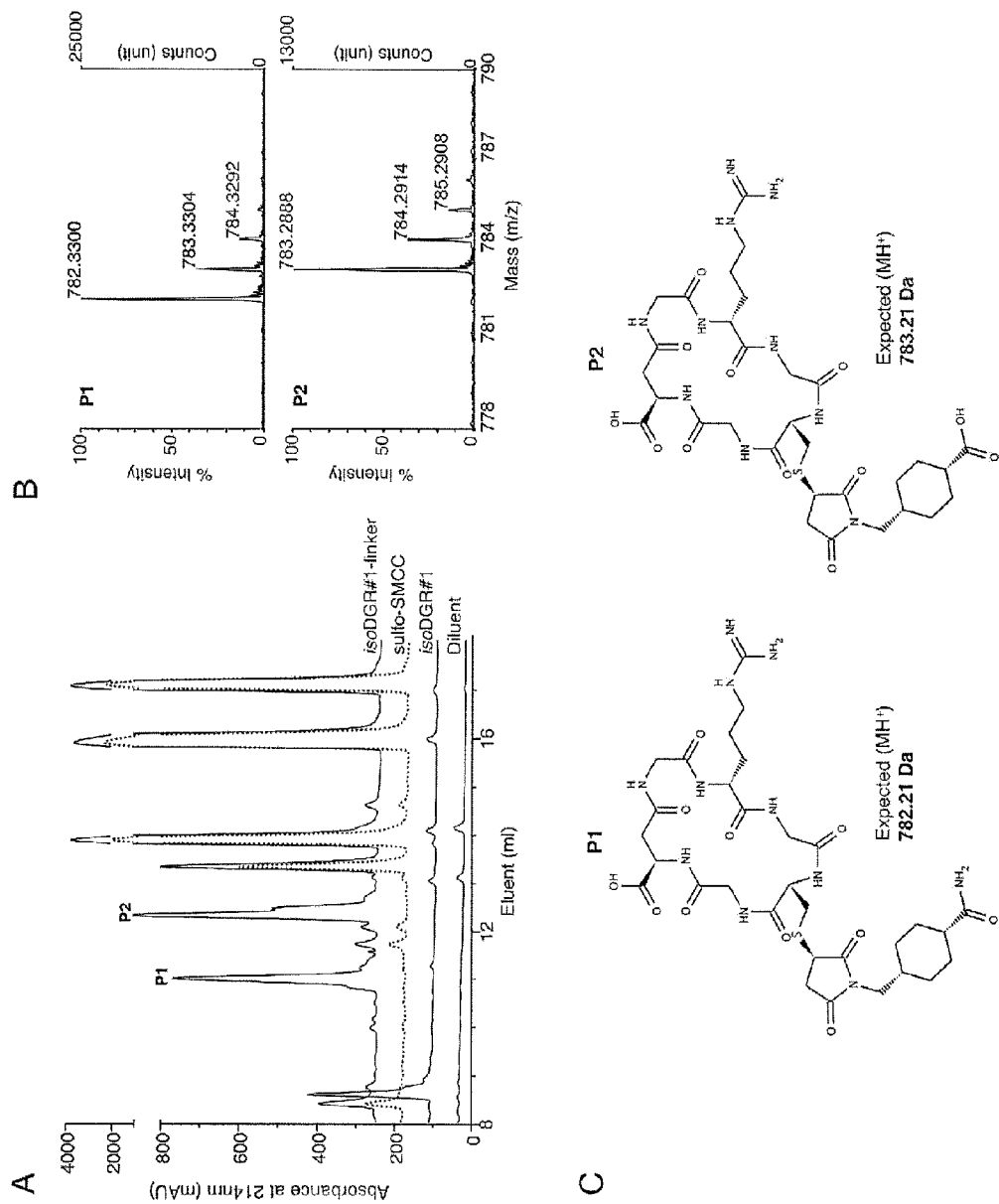

FIG. 3. Biochemical characterization of isoDGR#1-linker conjugate.

(A) RP-HPLC analysis of isoDGR#1 (10 μg), linker (sulfo-SMCC, 35 μg) and isoDGR#1-linker conjugate (10 μg) prepared as described in "Material and Methods" of Example 1.

(B) Mass spectrometry analysis (MALDI-TOF) of fractions corresponding to peak P1 and peak P2.

(C) Schematic representation of peptide-linker conjugates as deduced from monoisotopic masses.

Figure 4:
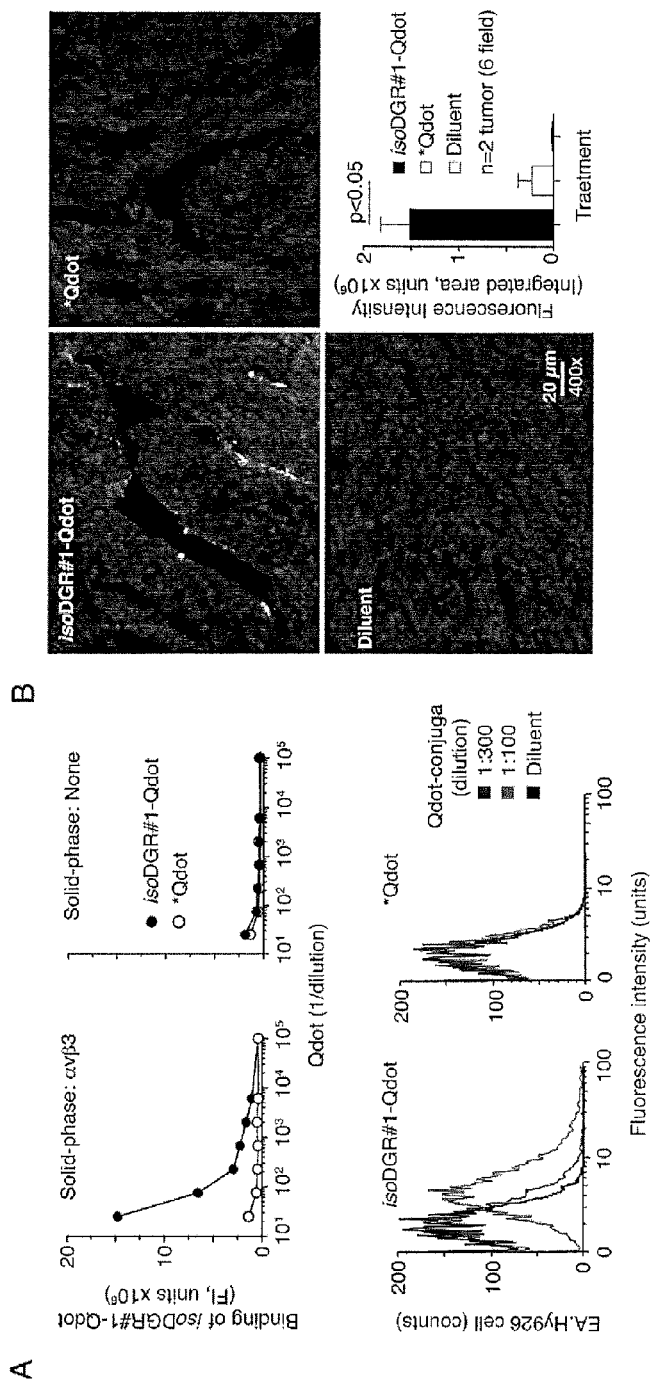

FIG. 4. LsoDGR#1-Qdot fluorescent nanoparticles binds αvβ3 on endothelial cells and homes to tumors.

(A) Binding of isoDGR#1-Qdot and linker-Qdot nanoparticles (*Qdot) to microtiter plates coated with human αvβ3 (upper panels) and to αvβ3-positive EA.hy926 cells (lower panels). Bound fluorescence was quantified using a Victor Wallac3 instruments (excitation filter, F355 nm; emission filter, 595/60 nM) (upper panels) and by FACS analysis (lower panels) as described previously [23].

(B) Homing of isoDGR-Qdot and *Qdot to WEH1-164 fibrosarcoma vasculature. Tumor were excised, 2 h after intravenous injection of isoDGR-Qdot, *Qdot or diluent (0.35 nmol/mice, 2 mice/group) and analyzed by fluorescence microscopy. Quantification of staining intensity was performed using the Adobe Photoshop CS3 software. Six images were analyzed for each condition. Magnification, 400×; red, Qdot; blue nuclear staining with DAPI; bar, 20 μm.

Figure 5:
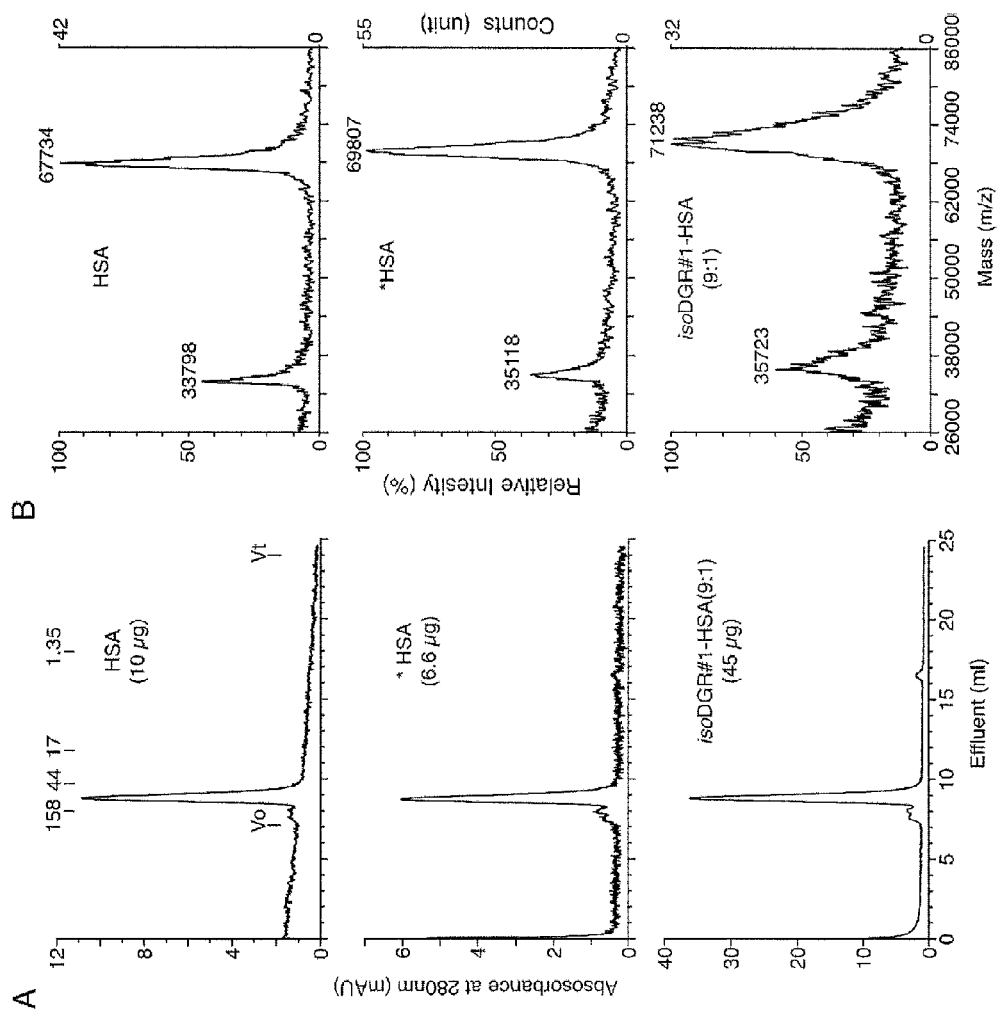

FIG. 5. Biochemical characterization of isoDGR#1-HSA (9:1) conjugate.

(A) Analytical gel filtration chromatography of HSA, linker-HSA (*HSA) and isoDGR#1-HSA (9:1) on a Superdex 75 HR column; void volume (Vo); total volume (Vt). The elution volume of molecular weight markers (158, 44, 17, 1.350 kDa) are shown.

(B) MALDI-TOF spectra of HSA, *HSA and isoDGR#1-HSA (9:1). IsoDGR#1-HSA consist of monomeric HSA modified with 6-7 linkers and 4-5 isoDGR#1 peptides.

Figure 6:
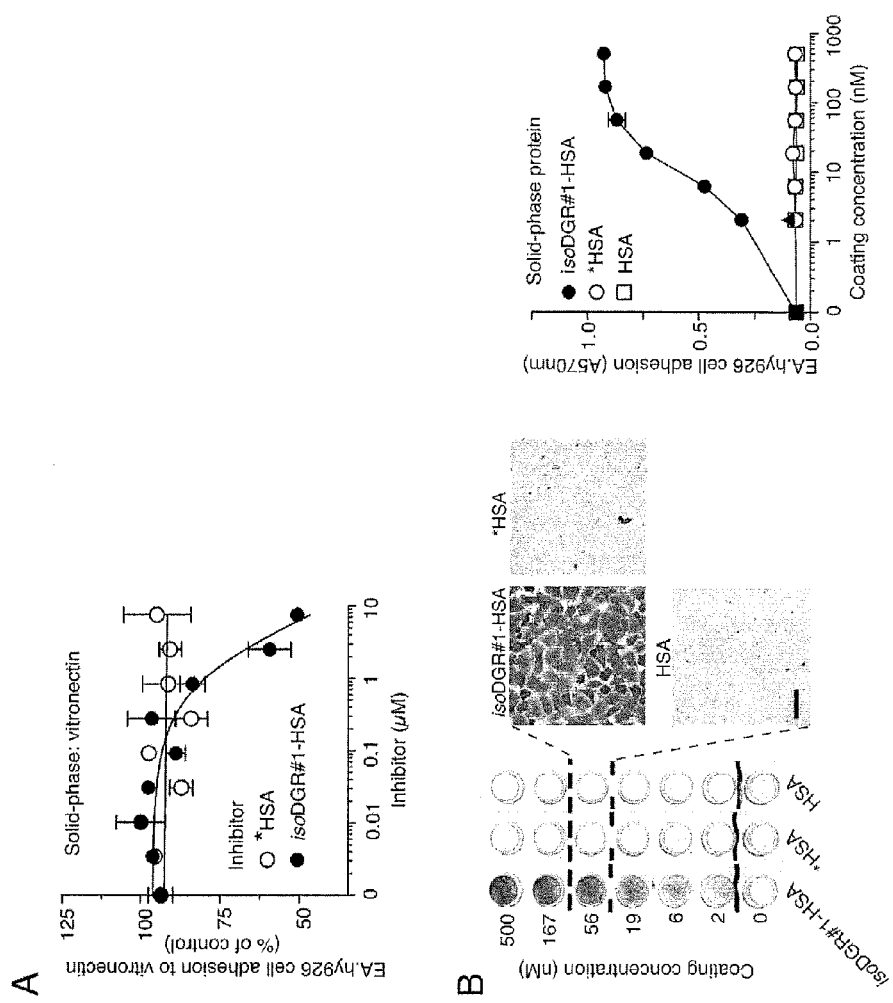

FIG. 6. IsoDGR#1-HSA affect endothelial cell adhesion in vitro.

(A) Endothelial EA.hy926 cell were mixed with isoDGR#1-HSA (9:1) and linker-HSA (*HSA), left to adhere for 2 h to microtiter plates coated with vitronectin and stained with crystal violet as described [23]. Cell adhesion was quantified by spectrophotometric measurement (A570 nm).

(B) EA.hy926 cell were left to adhere for 2 h to microtiter plate wells were coated with isoDGR#1-HSA (9:1), *HSA and HSA and stained with crystal violet. Left panels shows images and microphotographs of wells. Magnification, 400×; bar, 100 μm. Right panel shows the results of spectrophotometric quantification of cell adhesion. Mean±S.E (n=3).

Figure 7:
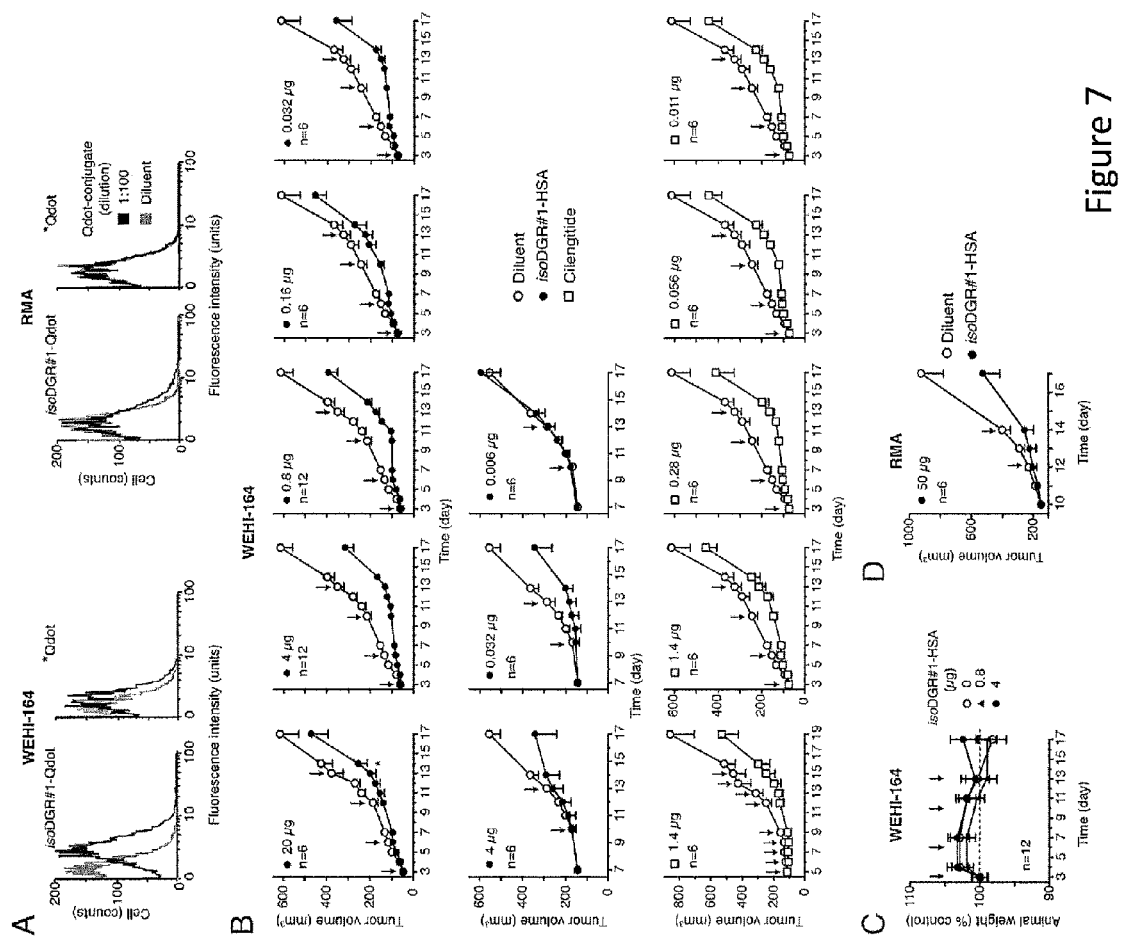

FIG. 7. IsoDGR#1-HSA and Cilengitide inhibit tumor growth in mouse models.

(A) Binding of isoDGR#1-Qdot and linker-Qdot (*Qdot) to WEHI-164 fibrosarcoma and RMA lymphoma cells as measured by FACS analysis.

(B-D) Mice bearing WEHI-164 fibrosarcomas and RMA lymphomas were treated (i.p.) with various doses of isoDGR#1-HSA (9:1) or Cilengitide as indicated. Arrows indicate the time of treatment. Tumor volumes are shown. Mean±S.E (6 or 12 mice/group).

Figure 8:
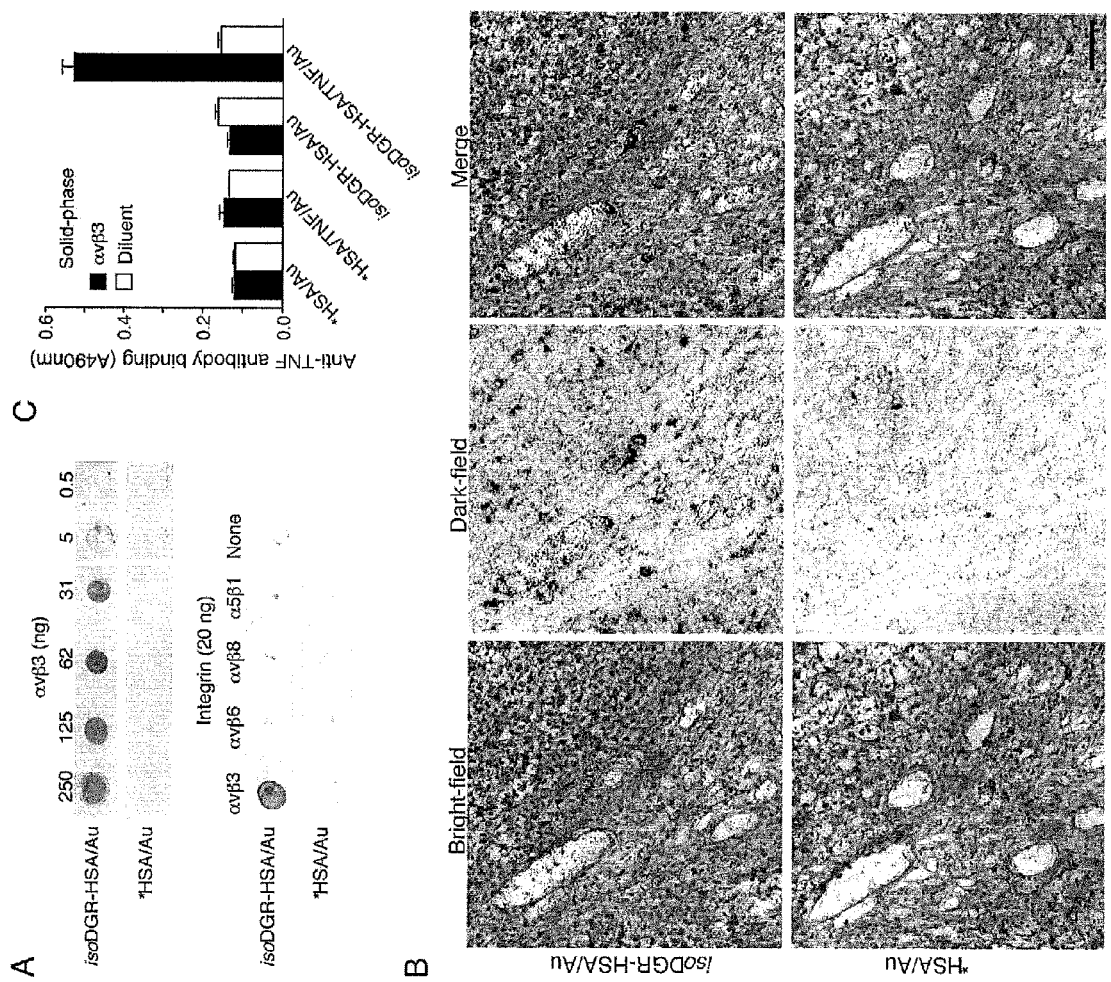

FIG. 8. Gold nanoparticles coated with isoDGR#1-HSA selectively bind the αvβ3 integrin.

(A) Binding of gold nanoparticles (20 nm) coated with isoDGR#1-HSA (isoDGR#1-HSA/Au) or linker HSA (*HSA/Au) to various amounts of αvβ3 and or other integrins spotted onto nitrocellulose filters (2 µl/spot). Gold nanoparticles were prepared as described in "Material and Methods" of Example 1, diluted 4-fold in 25 mM Tris-HCl, pH 7.4, containing 150 mM sodium chloride, 1 mM magnesium chloride, 1 mM manganese chloride, 1% BSA (binding buffer) and left to incubate with the filters 2 h, at r.t. The filters were washed with the same buffer and stained with Silver Enhancer Kit (Sigma).

(B) Binding of gold isoDGR#1-HSA/Au or *HSA/Au to WEHI-164 tumors tissue sections. Frozen tissue sections were incubated with PBS containing 3% BSA (1 h) and further incubated with isoDGR#1-HSA/Au or HSA/Au in binding buffer (2 h). The sections were washed and fixed with PBS containing 2% paraformaldehyde and 3% sucrose (15 min). After extensive washing with water, the sections were stained with the Silver Enhancer Kit and with hematoxylin. Sections were examined under dark- and bright-field illumination using a microscope (Carl Zeiss, Axiplan2). Dark filed images were color-inverted and merged with bright-filed images using the Adobe Photoshop CS3 software. Magnification, 100×; scale bar, 100 µm.

(C) Binding of gold nanoparticles coated with isoDGR#1-HSA and TNF (isoDGR#1-HSA/TNF/Au) or with *HSA and TNF (*HSA/TNF/Au) to αvβ3 integrin adsorbed onto microtiter plate. The binding was detected using a rabbit polyclonal anti-TNT antibody, followed by a goat anti-rabbit-HRP conjugate.

Figure 9:
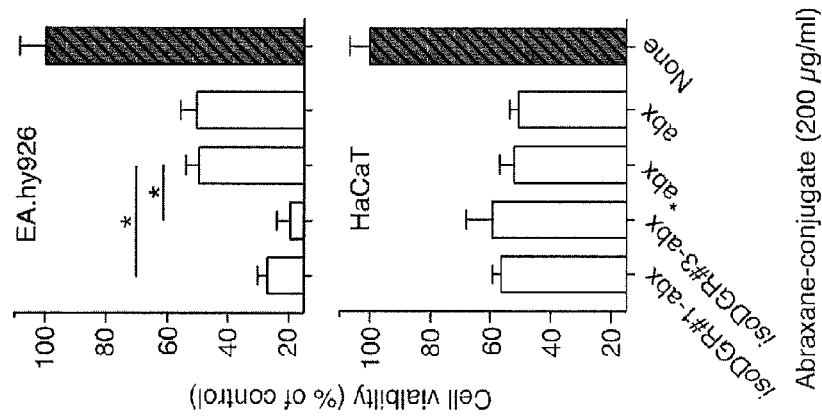

FIG. 9. Coupling isoDGR peptides to Abraxane improves its cytotoxic effect against αvβ3-positive endothelial cells, but not that against αvβ3-negative keratinocytes Abraxane was coupled to isoDGR#1 and isoDGR#3, as described in "Materials and Methods" of Example 1. The cytotoxic activity of Abraxane (abx), linker-Abraxane (*abx) and peptide-Abraxane conjugates was then tested using αvβ3-positive EA.hy926 endothelial cells and αvβ3-negative HaCat keratinocytes. Adherent cells were treated with 200 µg/ml of each conjugates overnight. Living cells were quantified by staining with solution (3-(4,5-dimethyl-2-thiazolyl)-2,5-diphenyl-2H-tetrazolium bromide (MTT).

Figure 10:
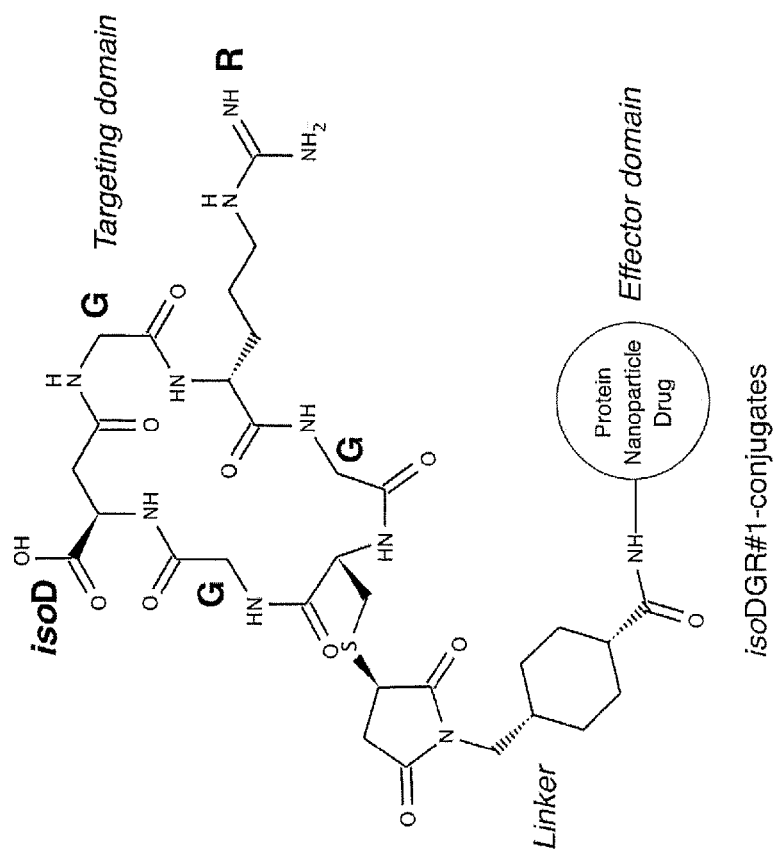

FIG. 10. Schematic representation of isoDGR#1-conjugates

The structure of the isoDGR#1-linker is shown. This product can be used to tag albumin and other compounds/nanoparticles to improve their tumor vasculature-homing properties.

Figure 11:
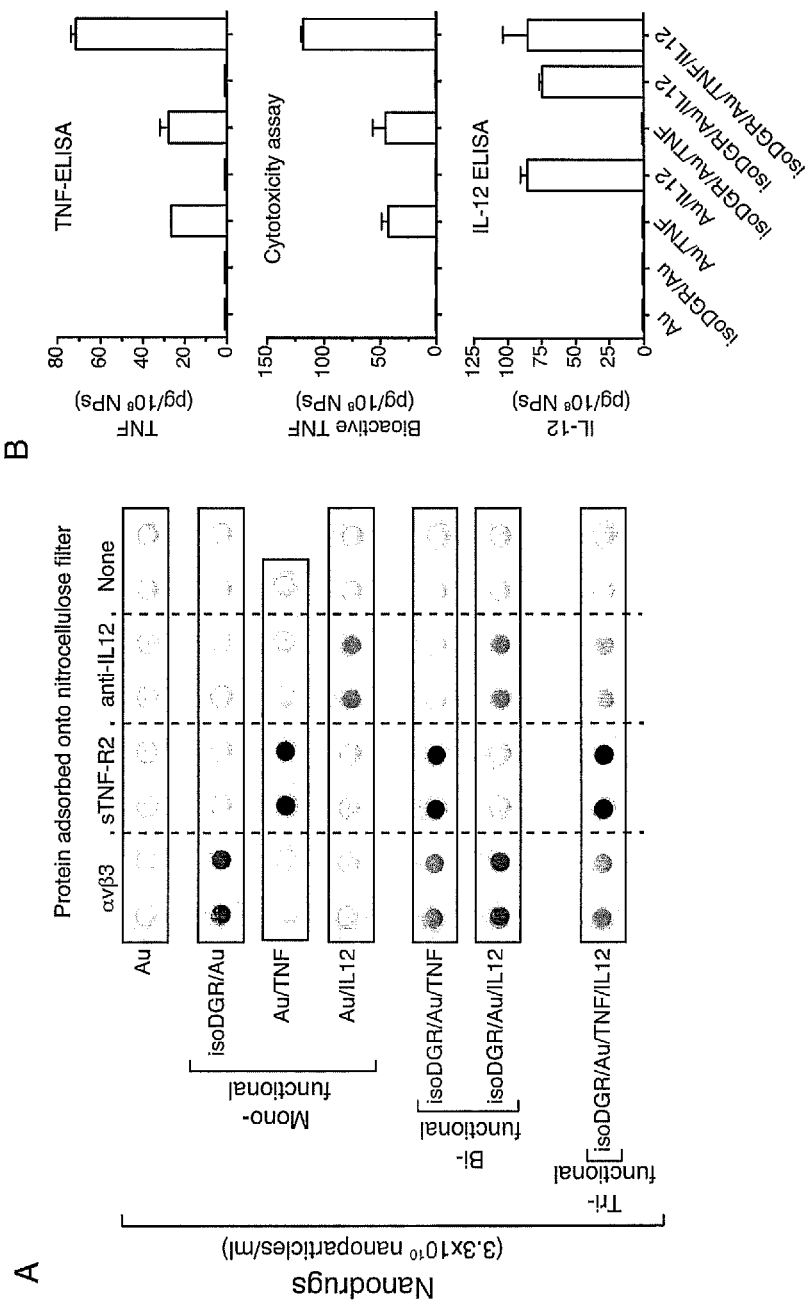

FIG. 11. Characterization of monofunctional, bifuctional and trifuctional nanodrugs.

(A) Binding of different nanodrugs (isoDGR/Au, Au/TNF, Au/12, isoDGR/Au/IL12, isoDGR/Au/TNF, isoDGR/Au/TNF/IL12) to αvβ3, soluble TNF receptor Type-II and anti-IL12 antibody adsorbed on a nitrocellulose filter as described in Example 2.

(B) Quantification of TNF bound to Au nanoparticles as described in Example 2 (by ELISA and cytotoxicity assay) and IL-12 (by ELISA). Nanoparticles (NPs).

Figure 12:
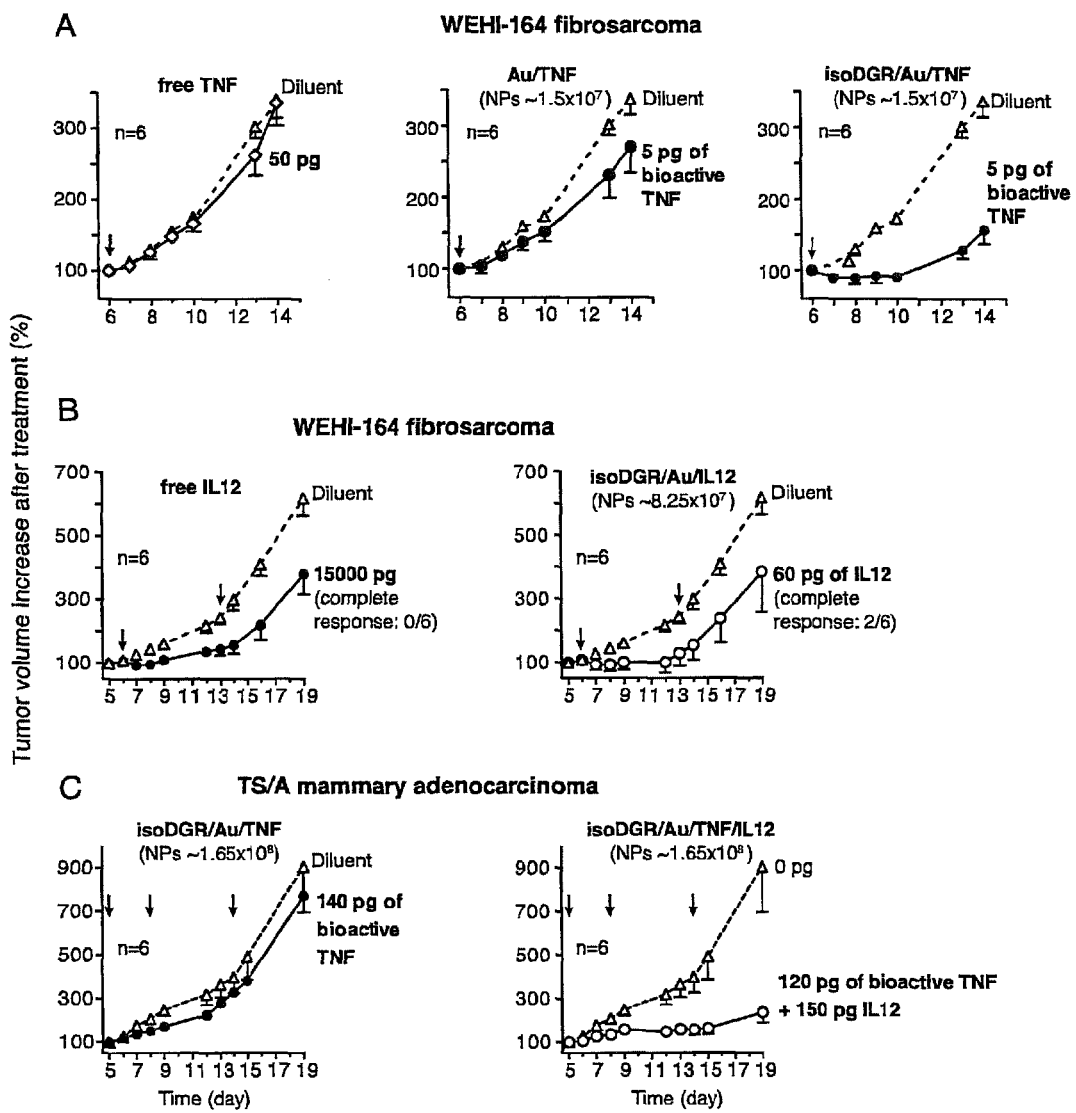

FIG. 12. Effect of free TNF, IL-12 and cytokine-bearing nanoparticles in tumor models characterized by different TNF sensitivity.

Tumor-bearing mice were treated with free TNF or IL-12 or cytokine-bearing nanoparticles as described in Example 2. Tumor models, number of injected nanoparticles (NPs) and amount of injected cytokines are reported in each panel. Tumor volumes after treatment is shown (mean±SE, 5-6 mice/group).

Figure 13:
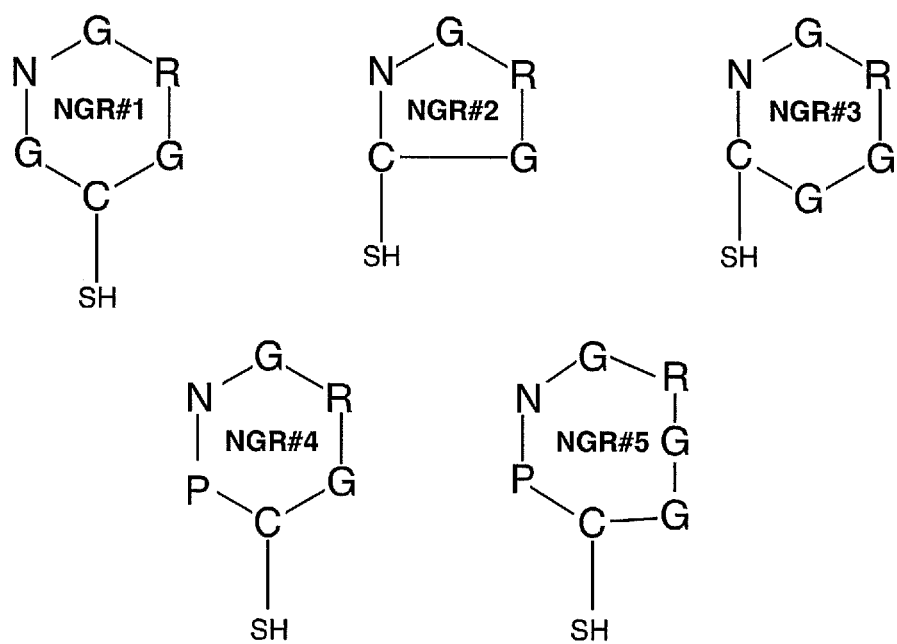

FIG. 13. Schematic representation of head-to-tail cyclic peptides.

Aminoacids are represented with the single letter code; SH, free thiol group. Peptide codes are reported within each structure.

Figure 14:
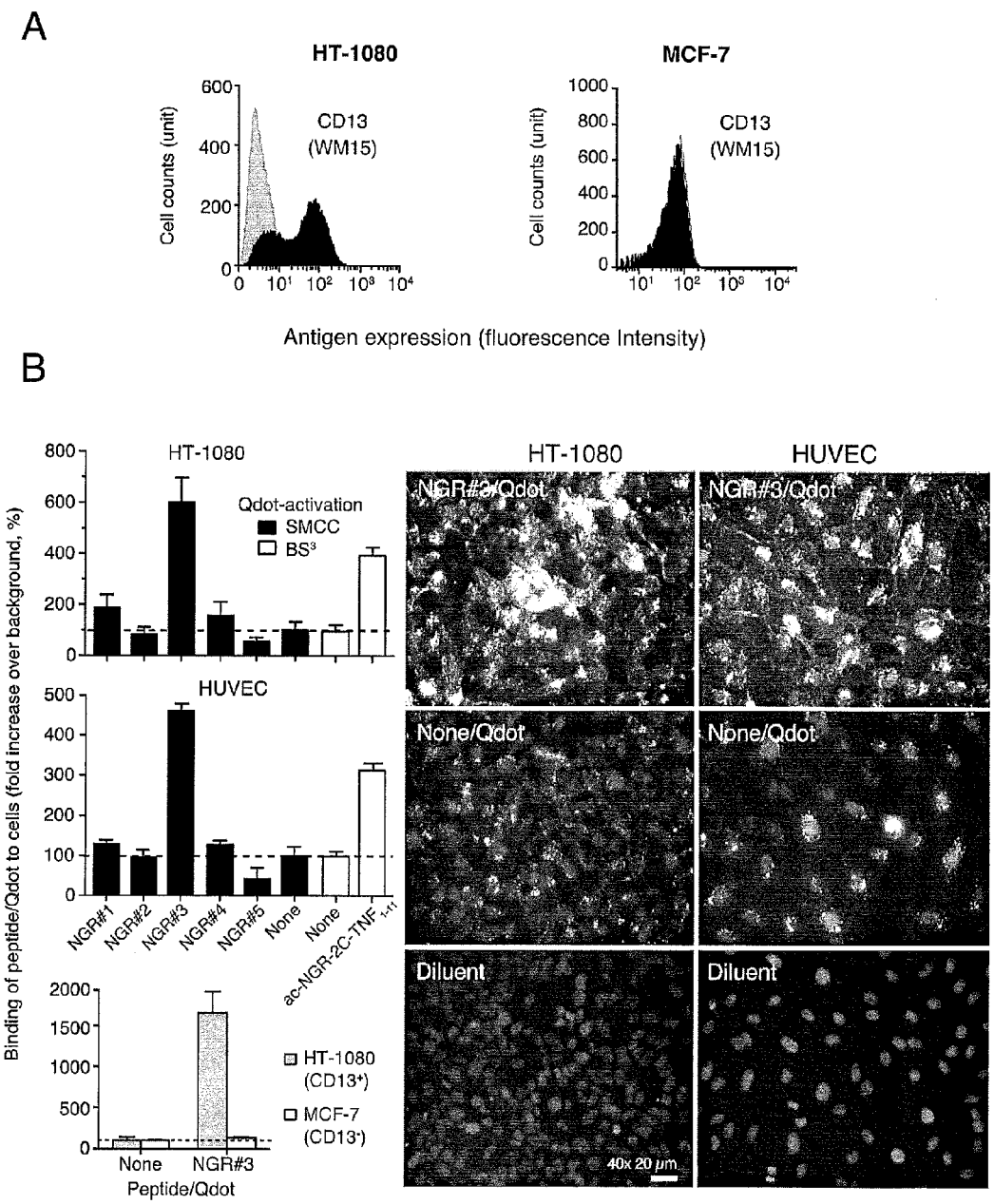

FIG. 14. NGR#3/Qdot binds to $CD13^+$ cells but not to $CD13^-$ cells.

(A) Expression of CD13 on human fibrosarcoma cells (HT-1080) and human breast adenocarcinoma cells (MCF-7), as evaluated by FACS analysis. FACS was carried out using mouse an anti human monoclonal antibodies (clone WM15, black histograms) followed by AlexaFluor 488-goat anti-mouse IgG polyclonal antibody. Controls cells (gray histograms) were incubated with AlexaFluor 488-goat anti-mouse alone.

(B) Binding of head-to-tail cyclized NGR peptides and disulphide constrained NGR peptide (ac-NGR-2C-TNF1-11, corresponding to acetylated-CNGRCGVRSSSRTPS-DKY) (SEQ ID NO:33) conjugated to fluorescent nanoparticles (Qdot) to HT-1080, human umbilical vein cells (HUVECs), and MCF-7 cells. NGR#/Qdots were prepared using the sulfo-SMCC linker (black, bars), whereas ac-NGR-2C-TNF1-11/Qdot were prepared using the BS3 linker (white, bars). Linker-Qdot, i.e. lacking the peptide, are indicated as None. Quantification of staining intensity was performed by using the Photoshop software. Six images were analyzed for each condition. Representative images are shown. Magnification, ×400; scale bar, 20 µm; red, Qdot; blue, nuclear staining with DAPI.

Figure 15:
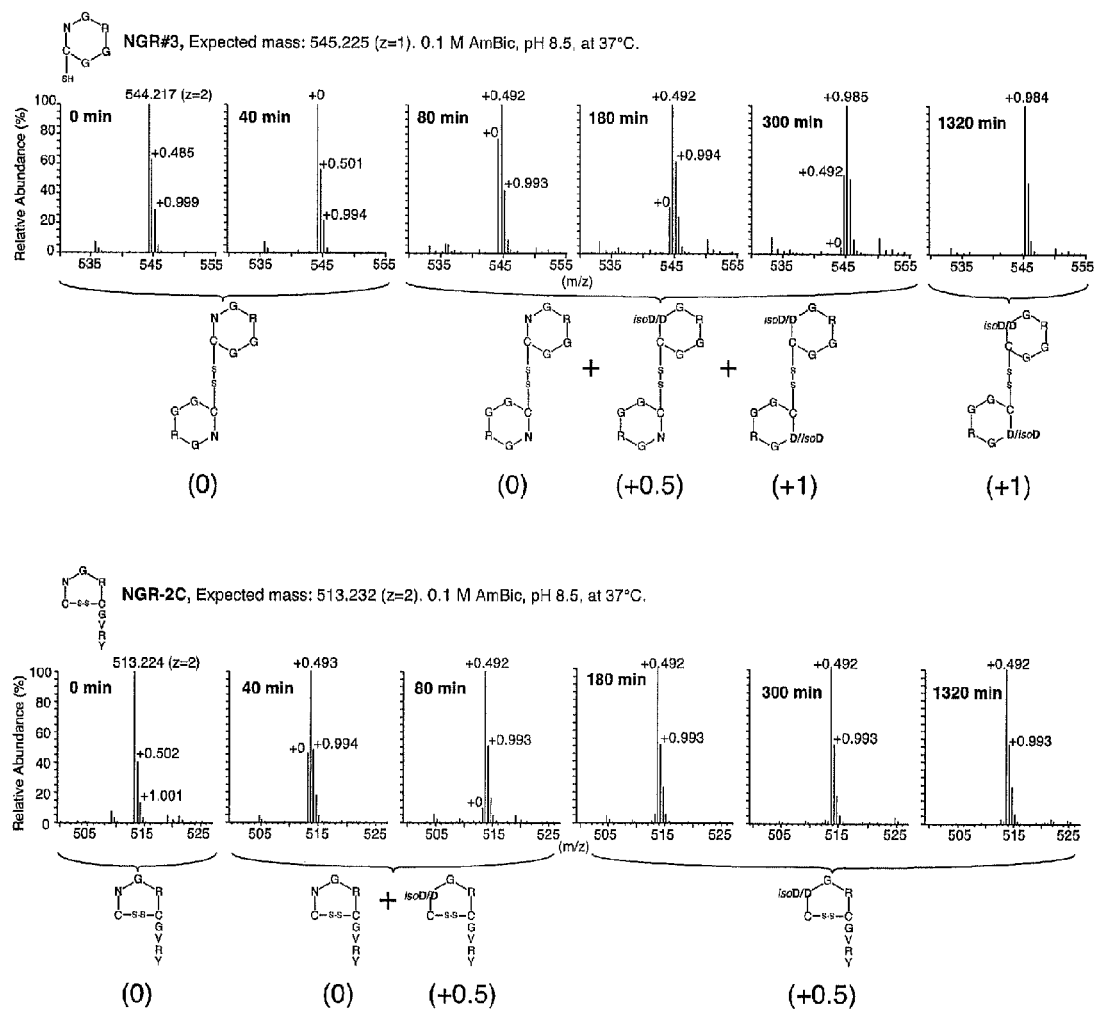

FIG. 15. Differential stability of head-to-tail cyclic and disulphide-constrained NGR peptides.

Orbitrap-ESI mass spectrometry analysis of NGR#3 and NGR-2C at various time points after incubation at 37° C. in 0.1 M ammonium bicarbonate buffer (Ambic), pH 8.5. During the analyses the NGR#3 forms dimers. +0 (no deamidation), +0.5 (one deamidation/molecule) and +1 (two deamidations/molecule) correspond to the difference between found and expected molecular masses in daltons. The results suggest that the molecular scaffold of NGR#3 reduce the deamidation rate.

Figure 16:
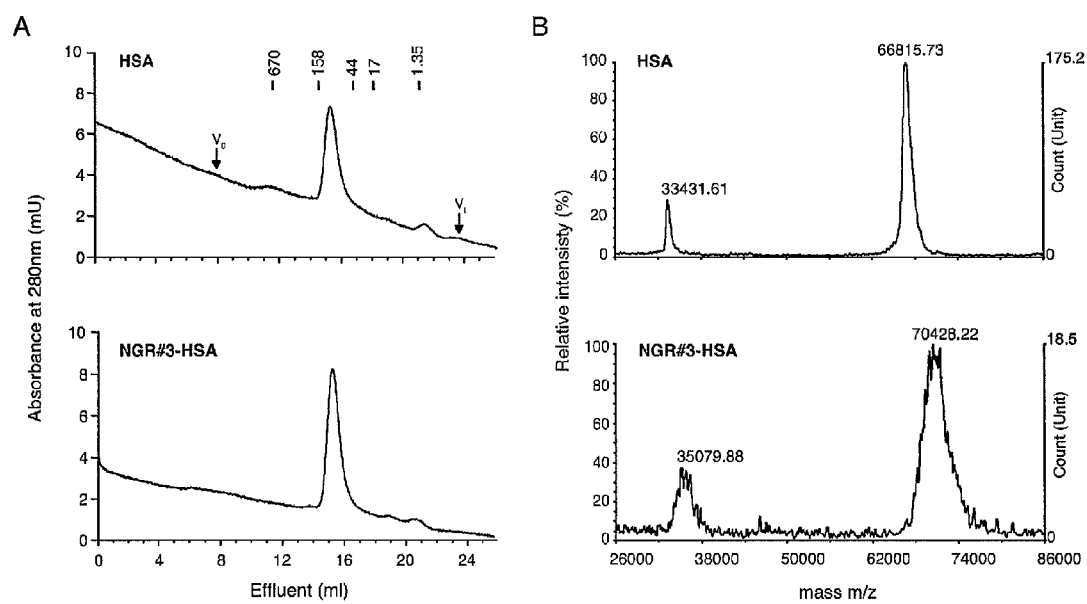

FIG. 16. Biochemical characterization of NGR#3-HSA conjugate.

(A) Analytical gel-filtration chromatography of HSA and NGR#3-HSA prepared with a 9:1 peptide/protein ratio, on a Superose 6 column Void volume (Vo), total volume (Vt); the elution volumes of molecular weight markers (670, 158, 44, 17, 1.350 kDa) are indicated.

(B) MALDI-TOF spectra of HSA and NGR#3-HSA (9:1). The results suggest that NGR#3-HSA consist of monomeric HSA modified with 4-5 peptides.

Figure 17:
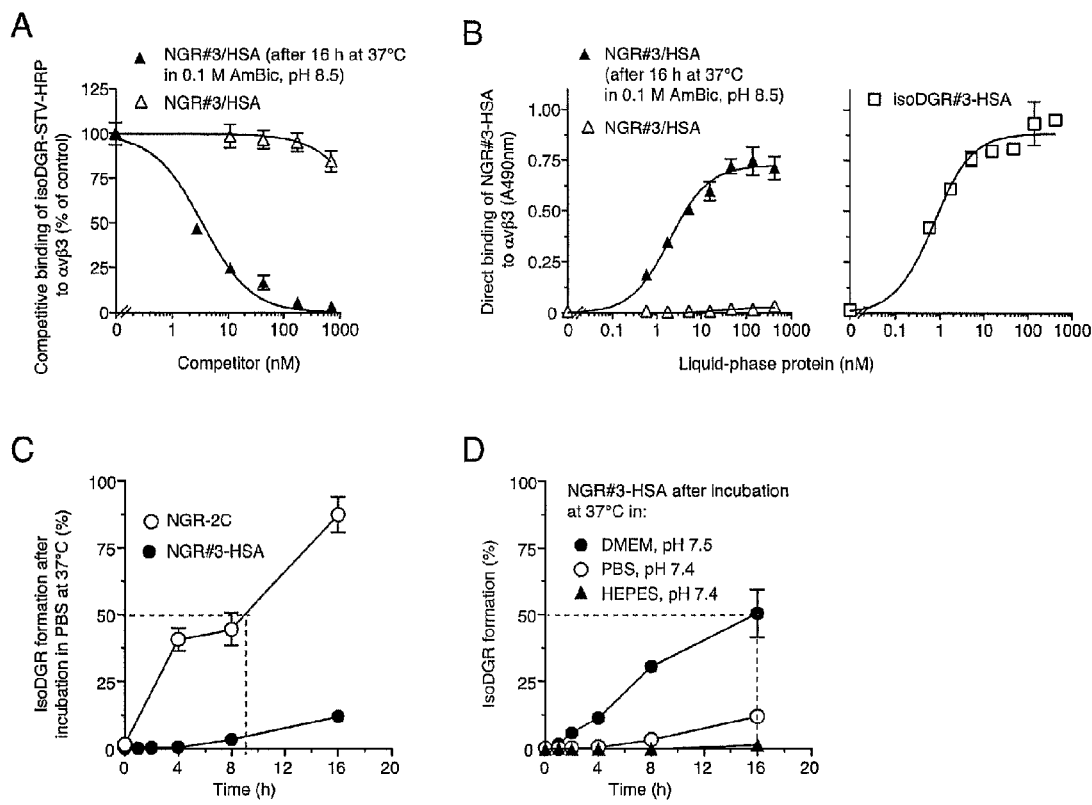

FIG. 17. Effect of accelerated aging of NGR#3-HSA on avb3 integrin recognition via isoDGR formation.

(A), (C) and (D) Competitive binding of biotinylated isoDGR-streptavidin peroxidase complexes (isoDGR-STV-HRP) to αvβ3-coated plates with NGR#3-HSA or NGR-2C after incubation in different buffers. The isoDGR content in NGR#3-HSA or NGR-2C (panel C and D) was quantified using the corresponding isoDGR peptides as reference standards and expressed as % of total peptide.

(B) Directed binding of NGR#3-HSA, before and after incubation in Ambic (B, left) and of isoDGR#3-HSA (B, right). The binding of was detected using an anti-human albumin polyclonal antibody, followed by a goat anti mouse-HRP conjugate.

EXAMPLES

Example 1

Materials and Methods

Cell Lines and Reagents

Human EA.hy926 endothelial cells, murine WEHI-164 fibrosarcoma cells and murine RMA lymphoma cells were cultured as described previously [28]. Human skin keratinocytes (HaCaT), kindly provided by Dr. Alessandra Boletta (San Raffaele Scientific Institute, Italy), were cultured in DMEM containing 10% fetal bovine serum, 50 µg/ml streptomycin and 100 U/ml penicillin. Human integrins α5β1, αvβ3 and αvβ5 were from Immunological Sciences (Rome, Italy); recombinant human integrins αvβ6 and αvβ8 were from R&D System (Minneapolis, Minn.). Sulfosuccinimidyl 4-[N-maleimidomethyl]cyclohexane-1-carboxylate (sulfo-SMCC) was from Pierce, Rockford, Ill. Human serum albumin (HSA) was from Baxter (Deerfield, Ill.); avidin was from BioSpa (Milan, Italy). Sodium phosphate buffer (10 mM, pH 7.4), containing 138 mM sodium chloride, 2.7 mM potassium chloride (PBS) was from Sigma-Aldrich (Milan, Italy). Abraxane® was from Abraxis BioScience (Herts, United Kingdom).

Peptide Synthesis

Figure 1:
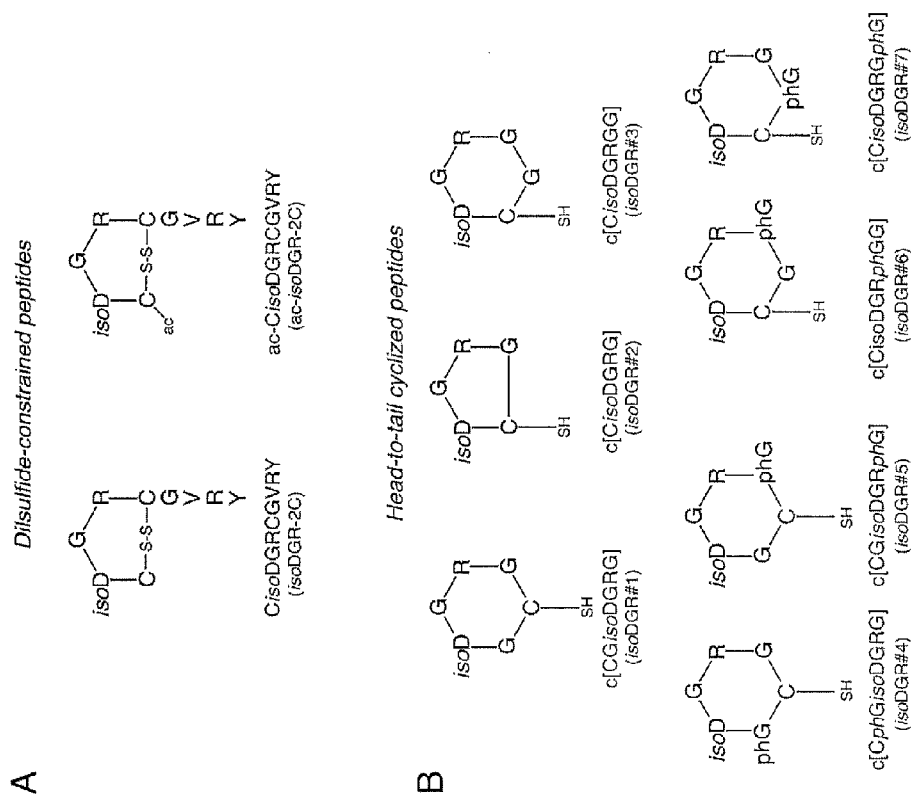
FIG. 1. Schematic representation of disulphide-constrained (A) and head-to-tail cyclized (B) peptides.

Disulphide-constrained CisoDGRCGVRY (SEQ ID NO:34) (isoDGR-2C) and acetyl-CisoDGRCGVRY (SEQ ID NO:35) (ac-isoDGR-2C) (FIG. 1A) were described previously [23]. Several head-to-tail cyclic peptides (see FIG. 1B for peptide sequence, code number and schematic representation) and cyclo(arginyl-glycyl-aspartyl-D-phenylalanyl-N-methyl-valyl (Cilengitide, an RGD head-to-tail cyclic pentapeptide selective for αvβ3 and αvβ5 integrins [13,14]), were prepared by the solid-phase Fmoc method [29]. All peptides were dissolved in water and stored in aliquots at −20° C. The molecular mass of each peptide was checked by MALDI-TOF mass spectrometry analysis.

Preparation of isoDGR-Linker Peptides isoDGR#1 and isoDGR#3 peptides (FIG. 1) (250 µg in 50 µl of water) were mixed with sulfo-SMCC (883 µg in 275 µl of PBS containing 5 mM EDTA) and left to incubate at room temperature for 3 h. Each solution was then mixed with 25 µl of 1 M ammonium chloride and left to incubate for 1 h at room temperature. Each product was then loaded onto a reverse-phase HPLC (RP-HPLC) C18 column (Prodigy ODS, 10 µm, 250×4.6 mm, PerSeptive Biosystem, Framingham, Mass.) connected to an AKTA purified HPLC (GE Healthcare). The column was then eluted as follows: mobile phase A, 0.1% trifluoroacetic acid in water; mobile phase B, 95% acetonitrile, 0.1% trifluoroacetic acid; 0% B for 4 min, linear gradient 0-100% B in 30 min, 100% B for 1 min, 0% of B for 6 min (flow rate, 0.5 ml/min). HPLC fractions were partially evaporated using a Savant SpeedVac System, to eliminate the organic phase.

Competitive Integrin Binding Assays

A conjugate consisting of biotinylated acetyl-CisoDGRCGVRSSSRTPSDKY (SEQ ID NO:36) peptide complexed with streptavidin-peroxidase conjugate (isoDGR/STV-HRP) was first prepared as described previously [23]. This conjugate, which recognizes the αvβ3, αvβ5, αvβ6, αvβ8 and α5β1 integrins [23], was then used in competitive binding assays with various isoDGR-containing peptides and conjugates as follows: isoDGR/STV-HRP was diluted with 25 mM Tris-HCl, pH 7.4, containing 150 mM sodium chloride, 1 mM magnesium chloride, 1 mM manganese chloride and 3% bovine serum albumin (BSA), and mixed with competitors. Each mixture was then added to microtiter plates coated with integrins (αvβ3, αvβ5, αvβ6, αvβ38, or α5β1) and incubated for 2 h at room temperature. After washing, each well was incubated with 70 µl of chromogenic solution (o-phenylenediamine dihydrochloride) for 20 min, at room temperature. The chromogenic reaction was stopped by adding an equal volume of 1 N sulfuric acid. The absorbance at 490 nm was then measured using a microtiter plate reader.

Coupling of isoDGR-Peptides to Qdot-Fluorescent Nanoparticles

Two nmoles of amino-modified quantum dots nanoparticles (Qdot) (Qdot605 ITK Amino (PEG), Invitrogen, Carlsbad, Calif.) were activated with sulfo-SMCC according to the manufacturer's instructions and purified by gel-filtration chromatography on NAP-5 column (GE Healthcare). The product (200 µl) was mixed with isoDGR-peptides (160 µg in 32 µl of water), or with water alone, and incubated for 2 h at room temperature. 2-mercaptoethanol was then added (0.1 mM, final concentration) and left to incubate for 0.5 h at room temperature. The peptide-Qdot conjugates were then purified by ultrafiltration (using Ultra-4 Ultracel-100K, Amicon), resuspended in 100 mM Tris-HCl, pH 7.4, and stored at 4° C.

Coupling isoDGR Peptides to Human Serum Albumin (HSA) and Avidin (AV).

All reactions were performed at room temperature. HSA (40 mg in 380 µl of PBS containing 5 mM ETDA) was mixed with sulfo-SMCC (2.4 mg in 120 µl of the same buffer), left to react for 1 h and purified by gel-filtration chromatography on NAP-5 column (GE Healthcare). Aliquots of activated HSA were mixed with various amounts of isoDGR-peptides (9:1, 3:1, 2:1 0:1 peptide/HSA molar ratio) and left to react for 3 h. Then, 2-mercaptoethanol was added (1 mM, final concentration) and left to incubate for 0.5 h. The conjugates were gel-filtered onto a PD10 column pre-equilibrated with PBS and stored at −20° C. Peptide-avidin coupling was carried out in the same manner using a peptide/protein molar ratio of 9:1.

In Vivo Studies

Studies in animal models were approved by the Ethical Committee of the San Raffaele Scientific Institute, and performed according to the prescribed guidelines. BALB/c (Harlan) or C57BL/6N mice (Charles River Laboratories), weighing 16 to 18 g, were challenged with s.c. injection in the left flank of $10^6$ WEHI-164 or $7\times10^4$ RMA living cells. Mice were injected, i.p., with various doses isoDGR-HSA conjugates or Cilengitide (100 µl) in 0.9% sodium chloride, containing 100 µg/ml HSA as a carrier. Tumor growth was monitored daily by measuring tumor volumes with calipers, as previously described [30]. Animals were sacrificed before tumors reached a diameter of 1.0 to 1.5 cm. Tumor sizes are shown as mean±SE (6 mice/group in each experiment).

Preparation of isoDGR#1-HSA-Tagged Gold Nanoparticles

IsoDGR#1-HSA or linker-HSA (*HSA), prepared with peptide/protein ratio 3:1 or 0:1, respectively, were adsorbed onto gold nanoparticles as follows: 57 µg of each conjugate (in 25 µl of 5 mM sodium citrate buffer, pH 6.0) were mixed with 250 µl of gold nanoparticles (20 nm, Sigma), left to incubate for 30 min at room temperature, mixed with 28 μl of 10% HSA and centrifuged twice (12000×g for 10 min). The final products, named isoDGR-HSA/Au and *HSA/Au, were resuspended with 25 mM Tris-HCl buffer, pH 7.4, containing 150 mM sodium chloride and 1% of HSA (250 μl final volume and stored at −80° C.

Nanoparticles loaded with isoDGR#1-HSA or *HSA and murine tumor necrosis factor-alpha (TNF-α) were prepared essentially as described above, except that gold nanoparticles (250 μl) were mixed with 28.5 μg of isoDGR#1-HSA (or *HSA) and 15 μg TNF. The final products were named isoDGR-HSA/TNF/Au and *HSA/TNF/Au, respectively.

Preparation of isoDGR-Tagged Abraxane

One vial of Abraxane (containing 100 mg of paclitaxel bound to albumin) was reconstituted with 20 ml of 0.9% sodium chloride. An aliquot (2.5 ml) of this solution was mixed with 200 μl of 10 mg/ml sulfo-SMCC and 250 μl of 500 mM sodium phosphate buffer, pH 7.4, containing 1500 mM sodium chloride and left to react for 30 min. The product was purified by gel-filtration chromatography on a PD-10 column (GE Healthcare). Aliquots (0.58 ml) of the product were mixed with isoDGR#1 and isoDGR#3 peptides (120 μl, 0.85 mg/ml), left to react overnight at 4° C., mixed with 2-mercaptoethanol (1 mM, final concentration) and further incubated for 0.5 h at room temperature. The conjugates were ultrafiltered (cut off, 10000 Da) and tested by cytotoxicity assays using EA.hy926 endothelial cells and HaCat keratinocytes.

Results

Identification of αvβ3/αvβ5-Selective isoDGR Peptides Containing a Free Thiol Group We have prepared various head-to-tail-cyclized isoDGR peptides (5-6 residues) containing a single Cys (FIG. 1B). The binding affinity and selectivity of each peptide for different integrins were then analyzed by competitive binding assay, using αvβ3-, αvβ5-, αvβ6-, αvβ8- and α5β1-coated plates and isoDGR/STV-HRP, an ac-isoDGR-2C/peroxidase complex, as competitor. The results showed that the peptide molecular scaffold markedly contributes to integrin recognition and selectivity (Table 1). For example, the peptide c(CisoDGRGG) (SEQ ID NO:30) (called isoDGR#3) could bind αvβ3, αvβ5, αvβ6, αvβ8 and α5β1 with similar affinity, whereas the peptide c(CGisoDGRG) (SEQ ID NO:1) (called isoDGR#1) was more selective for αvβ3 and αvβ5. Furthermore, replacement of the first glycine of isoDGR#1 with a D-phenylglycine (as in peptide isoDGR#4) markedly reduced the affinity for αvβ3 and αvβ5 and increased the affinity for αvβ6, αvβ8 and α5β1 (Table 1). Both isoDGR#1 and isoDGR#3 could efficiently inhibit endothelial cell adhesion, although with a different potency (FIG. 2), data suggesting that these peptides can bind integrins also on the endothelial cell surface. isoDGR#1 and #3 were selected for further studies, as representatives of "selective" and "non-selective" peptides.

Coupling isoDGR-Peptides to Sulfo-SMCC Enhances their Integrin Binding Affinity and Selectivity The free thiol-group of isoDGR#1 and #3 enables peptide conjugation to aminogroup-containing compounds (e.g. HSA) by using sulfo-SMCC, an efficient and widely used cross-linking reagent. To assess the effect of this linker on integrin recognition, we prepared peptide-linker conjugates and, after blocking reactive sulfo-succinimide group with ammonium chloride, we analyzed their integrin binding properties. HPLC and mass spectrometry analysis of the isoDGR#1-linker conjugate showed the presence of two components, called P1 and P2, that correspond to conjugates with an amido- or carboxylic-group, respectively (FIGS. 3A, B and C), likely owing to partial hydrolysis of sulfo-succinimide during the blocking step. Similar results were obtained also with the isoDGR#3-linker conjugate (not shown).

Integrin binding studies performed with these isoDGR#1-linker conjugates showed an improved binding affinity and selectivity for αvβ3 and αvβ5 in both cases, compared to the free peptide (see Table 1 and Table 2). Notably, the linker improved also the selectivity isoDGR#3, despite the free peptide was non-selective at all, suggesting that the linker somehow contributed to integrin recognition. Notably, the highest selectivity for αvβ3 and αvβ5 was obtained with the isoDGR#1-linker conjugate. Thus, this product was selected for further studies.

IsoDGR#1-Linker Conjugate can Home to the Tumor Vasculature

To assess whether the isoDGR#1-linker conjugate can recognize endothelial cells in vivo we coupled isoDGR#1 to sulfo-SMCC-activated Qdot (*Qdot) fluorescent nanoparticles. This conjugate maintained the capability to bind the purified αvβ3-integrin and αvβ3-positive endothelial cells in vitro (FIGS. 4A and B). The isoDGR#1-Qdot nanoparticles were then injected into WEHI-164 tumor-bearing mice and left to circulate for 2 h. The tumors were excised and analyzed by fluorescence microscopy. A stronger staining of vessels was observed in tumors treated with isoDGR#1-Qdot, compared to *Qdot (nanoparticles with linker, but lacking the peptide) (FIG. 4C), data suggesting that the isoDGR#1-linker moiety can recognize endothelial cells in vivo and that it can be exploited for the generation of nanoparticles that home in on tumor vessels.

Coupling of isoDGR#1-Linker to Albumin Increases Peptide Affinity and Selectivity for αvβ3

Next, we coupled isoDGR#1 to sulfo-SMCC-activated albumin (*HSA) using different peptide/protein ratio. Gel-filtration chromatography of isoDGR#1-HSA, prepared with a 9:1 peptide/protein ratio, revealed a main peak with a hydrodynamic size similar to that of HSA and *HSA (FIG. 5A). Mass spectrometry analysis of HSA, *HSA and isoDGR#1-HSA revealed average molecular masses of 67734, 69807 and 71238, respectively, suggesting that isoDGR#1-HSA mainly consist of monomeric HSA modified with 6-7 linkers and 4-5 isoDGR#1 peptides (FIG. 5B).

Integrin binding assays showed that albumin increased both affinity and selectivity of isoDGR#1 for αvβ3 (Table 3). For example, the αvβ8/αvβ3 Ki ratio, which was 70 in the case of free isoDGR#1 (Table 1), increased to 3028 after conjugation to HSA (Table 3). This suggest that the affinity of the conjugate for αvβ3 is >3000-fold higher than that for αvβ8.

Also the selectivity of isoDGR#3 and #5 for αvβ3 markedly increased after coupling to HSA, (Table 3), suggesting that both linker and HSA moieties contribute to integrin binding selectivity. Enhancement of isoDGR#1 affinity and selectivity (although to a different extent) was observed also when avidin was used in place of HSA (Table 3). These data, overall suggest that both linker and protein scaffold contribute to integrin recognition by isoDGR peptides and that the isoDGR#1-HSA conjugate was the most selective composition for αvβ3.

Notably, the selectivity of isoDGR#1-HSA for αvβ3 was superior to that of Cilengitide, an RGD-containing antagonist of αvβ3, which is being tested in cancer patients as an anti-angiogenic/anti-cancer drug (Table 3). For example, the αvβ8/αvβ3 Ki ratios for isoDGR#1-HSA (9:1) and Cilengitide, were 3028 and 122, respectively. Higher Ki ratios were observed also with the other integrins (Table 3).

IsoDGR#1-HSA Binds Endothelial Cells and Affects their Adhesion In Vitro

The interaction of isoDGR#1-HSA with endothelial cells was then investigated using in vitro cell adhesion assays. Soluble isoDGR#1-HSA, added to the cell supernatant, could efficiently inhibit EA.hy926 endothelial cell adhesion mediated by solid-phase vitronectin, a ligand of αvβ3 (FIG. 6A). In contrast, sulfo-SMCC-activated HSA (*HSA) was completely inactive. In another assay, based on solid-phase isoDGR#1-HSA, this conjugate promoted cell adhesion and spreading (FIG. 6B). These data suggest that isoDGR#1-HSA binds to endothelial cells and affect their adhesion properties.

The isoDGR#1-HSA Inhibits Tumor Growth In Vivo

αvβ3-mediated cell adhesion is crucial for endothelial cell survival and proliferation in tumors and, therefore, for angiogenesis and tumor growth [11,31-33]. This notion led us to investigate whether isoDGR#1-HSA might affect tumor growth in WEHI-164-fibrosarcoma and RMA-lymphoma bearing-mice. FACS analysis of these tumor cells showed that WEHI-164, but not RMA cells, expresses the αv-integrin subunit (data not shown). Accordingly, isoDGR#1-Qdot could bind WEHI-164, but not RMA cells, in vitro as assessed by FACS analysis (FIG. 7A).

In vivo experiments performed with the WERE-164 model showed that a wide range of doses of isoDGR#1-HSA (from 0.032 to 20 μg) could delay tumor growth when administered biweekly (i.p.) to mice (FIG. 7B). No loss of body weight or toxicity was observed at any of the tested doses (FIG. 7C). A similar behavior was observed also with cilengitide, a monovalent RGD peptide selective for αvβ3 (FIG. 7B, lower panels). These results suggest that both isoDGR#1-HSA and Cilengitide can delay the growth of the WERE-164 tumors to a similar extent. In both cases the effect was lasting no more than 5-6 days and increasing dose or the frequency of treatment did not increase the effect.

IsoDGR#1-HSA could induce anti-tumor effects also in the RMA-lymphoma model (FIG. 7D). Given that RMA cells do not bind isoDGR#1 peptide (FIG. 7A), this result supports the hypothesis that elements of the tumor microenvironment, presumably endothelial cells, are important targets of isoDGR#1-HSA.

IsoDGR#1-HSA can be Exploited for the Preparation of αvβ3-Selective Nanoparticles Then, we explored the utility of isoDGR-tagged albumin for the preparation of nanoparticles and nanomedicines with improved selectivity for αvβ3-positive vessels.

Considering that colloidal-gold nanoparticles represent an interesting platform for the preparation of nanomedicines and theragnostics [34-36], we have adsorbed isoDGR#1-HSA onto 20 nm gold nanoparticles (Au) and analyzed their integrin binding properties. An isoDGR#1-HSA/Au conjugate, but not a conjugate lacking isoDGR (*HSA/Au), could bind with a good selectivity the integrin αvβ3 spotted onto nitrocellulose filters (FIG. 8A). IsoDGR#1-HSA/Au could also bind tumor vessels more efficiently than *HSA/Au in WEHI-164 tumor tissue sections (FIG. 8B). To assess whether isoDGR-HSA/Au can be exploited as a new platform the preparation of nanomedicines we have simultaneously loaded gold nanoparticles with isoDGR-HSA and TNF, a well known anticancer drug [37,38], and tested their ability to bind αvβ3 and anti-TNF antibodies by sandwich ELISA. The results showed that these new particles could indeed form molecular sandwiches with αvβ3 and anti-TNF antibodies, indicating that both isoDGR-HSA and TNF were present (FIG. 8C). In conclusion, these results suggest that isoDGR#1-HSA can maintain its integrin binding selectivity even after adsorption onto gold nanoparticles. Thus, isoDGR-HSA/Au can be exploited as a new platform for the preparation of new gold-based nanomedicines with improved selectivity for tumor vessels.

Coupling isoDGR#1 to Abraxane Improves its Cytotoxic Activity Against αvβ3-Positive Cells Abraxane is an albumin-paclitaxel nanoparticle approved for the treatment of metastatic breast cancer (www.abraxane.com). Coupling Abraxane to isoDGR#1 and isoDGR#3 improved its cytotoxic activity against αvβ3-positive EA.hy926 endothelial cells, but not against αvβ3-negative HaCat keratinocytes (FIG. 9). These results further support the hypothesis that isoDGR#1 can be exploited for the preparation of albumin-based nanoparticles with improved ability to recognize endothelial cells.

Example 2

Development of TNF- and IL-12-Based Nanodrugs Functionalized with Cyclic IsoDGR Peptide Materials and Methods Reagents Human serum albumin (HSA) was from Baxter (Deerfield, Ill.); bovine serum albumin (BSA) was from Sigma. Murine tumor necrosis factor-alpha (TNF) was prepared as described previously [46], murine interleukin-12 (IL12) was from Peprotec. TNF and IL-12 were dialyzed against 5 mM citrate buffer, pH 6.0 and stored at 20° C. in aliquots.

Sodium phosphate buffer (10 mM, pH 7.4), containing 138 mM sodium chloride, 2.7 mM potassium chloride (PBS) and normal goat serum (NGS) were from Sigma-Aldrich (Milan, Italy).

Cyclic head-to-tail c(CGisoDGRG) (SEQ ID NO:1) peptide (isoDGR#1 shown in FIG. 1) was prepared and characterized as described in the "Materials and Methods" of Example 1.

Coupling isoDGR Peptides to Human Serum Albumin.

All reactions were performed at room temperature. HSA, 40 mg in 380 μl of PBS containing 5 mM EDTA (PBS-E) was mixed with sulfo-SMCC (2.4 mg in 120 μl in water), left to react for 1 h and purified by gel-filtration chromatography on NAP-5 column. Aliquots of activated-HSA (20 mg) were mixed with isoDGR#1 (1.5 mg, 9:1 peptide/HSA molar ratio) and left to react for 3 h. Then, 2-mercaptoethanol was added (1 mM, final concentration) and left to incubate for 0.5 h. The conjugates were gel-filtered through a PD10 column pre-equilibrated with PBS and stored at −20° C. The product was called isoDGR#1-HSA.

Preparation of isoDGR#1-HSA-Tagged Gold Nanoparticles (isoDGR/Au)

isoDGR#1-HSA was coupled to gold nanoparticles as follows: 60 μg of isoDGR#1-HSA (in 25 μl of 5 mM sodium citrate buffer, pH 6.0) were mixed with 500 μl of gold nanoparticles (25 nm-gold nanoparticles, Aurion, The Netherland), and left to incubate for 1 h at room temperature under shaking. Then, 100 μl of mPEG-SH solution (15 μg/ml in water, MW 20000, NANOCS) was added to the mixture and left to incubate for 15 min at room temperature. Finally, 112 μl of 10% HSA (in water) was added to saturate gold nanoparticles. The mixture was centrifuged twice (14000×g for 15 min). The final product, named isoDGR/Au, was resuspended with 5 mM sodium citrate buffer, pH 6.0, containing 1% HSA to 500 μl final volume and stored at 4° C.

Preparation of isoDGR/Au Nanoparticles Loaded with IL-12 (isoDGR/Au/IL12)

Bifunctional gold nanodgrus loaded with isoDGR#1-HSA and IL-12 were prepared as follows: 121.24 µg of isoDGR#1-HSA were mixed with 1.276 µg of IL-12 in 60 µl of 5 mM sodium citrate buffer, pH 6.0. The mixture was then added to 1 ml of 25 nm-gold nanoparticles and left to incubate for 1 h at room temperature under shaking. Then, 100 µl of mPEG-SH solution was added to the mixture and left to incubate for 15 min at room temperature. Finally, 112 µl of 10% HSA was added to saturate gold nanoparticles. The mixture was centrifuged twice (14000×g for 15 min) The final product, named isoDGR/Au/IL12, was resuspended with 5 mM sodium citrate buffer, pH 6.0, containing 1% HSA to 500 µl final volume and stored at 4° C.

Preparation of isoDGR/Au Nanoparticles Loaded with TNF (isoDGR/Au/TNF)

Bifunctional nanoparticles loaded with isoDGR#1-HSA and TNF were prepared as follows: 80 µg of isoDGR#1-HSA were mixed with 8 µg of TNF in 60 µl of 5 mM sodium citrate buffer, pH 6.0. The mixture was then added to 1 ml of 25 nm-gold nanoparticles and processed as describe above for isoDGR/Au/IL-12. The final product, named isoDGR/Au/TNF.

Preparation of isoDGR/Au Nanoparticles Loaded with TNF and IL-12 (isoDGR/Au/TNF/IL12)

Trifunctional nanoparticles loaded with isoDGR#1-HSA, IL-12 and TNF were prepared as follows: 132 µg of isoDGR#1-HSA were mixed with 1.745 µg of IL-12 and 7.660 µg of TNF in 90 µl of 5 mM sodium citrate buffer, pH 6.0. The mixture was then incubated with gold nanoparticles and processed as described above. The final product was named isoDGR/Au/TNF/IL12.

Characterization of Monofunctional, Bifunctional and Trifuctional Nanodrugs

Binding of different nanodrugs (isoDGR/Au, Au/TNF, Au/12, isoDGR/Au/IL12, isoDGR/Au/TNF, isoDGR/Au/TNF/IL12) to αvβ3, soluble TNF receptor Type-II and anti-IL12 antibody adsorbed on a nitrocellulose filter was investigated. Nitrocellulose filters were coated with αvβ3 (25 ng/spot), soluble TNF receptor Type-II (sTNF-R2, 250 ng/spot) or anti-IL12 monoclonal antibody (250 ng/spot). The filters were incubated with 25 mM Tris-HCl, pH 7.4, containing 150 mM sodium chloride, 1 mM magnesium chloride, 1 mM manganese chloride, 1% BSA for 30 min. Then $3.3\times10^{10}$ nanoparticle/ml of each conjugate were diluted in the same buffer, added to the filters and left to incubate for 2 h at room temperature. The filters were then washed with the same buffer, rinsed with water for 5 min and stained with Silver Enhancer Kit (Sigma).

Quantification of TNF Bound to Au Nanoparticles (by ELISA and Cytotoxicity Assay) and IL-12 (by ELISA). Nanoparticles (NPs).

The amount of IL-12 or TNF bound to nanoparticles was estimated by IL-12- and TNF-ELISAs. Bioactive TNF bound to nanoparticles was measured by LM-cell cytotoxicity assay [46].

TNF-ELISA was carried out using the rat anti-murine TNF mAb V1q (capture antibody) and a rabbit anti-TNF polyclonal antiserum (detection antibody), followed by polyclonal goat anti rabbit-HRP conjugate.

IL12-ELISA was carried out using the anti-IL-12/IL-23 p40 mAb C15.6 (capture antibody, Biolegend) and biotinylated anti-IL-12/IL-23 p40 mAb C17.8 (detection antibody, Biolegend) followed by streptavidin-HRP conjugate (R&D System).

In Vivo Studies

Studies in animal models were approved by the Ethical Committee of the San Raffaele Scientific Institute, and performed according to the prescribed guidelines. BALB/c or C57BL/6N mice (Charles River Laboratories), weighing 16 to 18 g, were challenged with s.c. injection in the left flank of $10^6$ WEHI-164 or $2\times10^5$ TS/A living cells. Mice were injected, i.v., with freshly prepared nanodrugs, diluted with the same diluent. Tumor growth was monitored daily by measuring tumor volumes with calipers, as previously described. Animals were sacrificed before tumors reached a diameter of 1.0 to 1.5 cm. Tumor sizes are shown as mean±SE (6 mice/group in each experiment).

Results

Preparation of Monofunctional, Bifuctional and Trifunctional Nanodrugs Bearing isoDGR-HSA, IL-12 and/or TNF.

To assess the functional properties of isoDGR-HSA, TNF and IL-12 after coupling to Au nanoparticles we studied the binding of isoDGR/Au, Au/TNF, Au/12, isoDGR/Au/IL12, isoDGR/Au/TNF, isoDGR/Au/TNF/IL12 to αvβ3, soluble TNF receptor Type-II and anti-IL12 antibody adsorbed on a nitrocellulose filter. The results, reported in FIGS. 11A and B, shows that the three components maintain their functional properties after coupling to gold.

Anti-Tumor Activity of Bifuctional and Trifunctional Nanodrugs Bearing isoDGR-HSA, EL-12 and/or TNF.

The anti-tumor activity of bifuctional and trifunctional nanodrugs bearing isoDGR-HSA, IL-12 and/or TNF was then investigated using two tumor models characterized by different TNF sensitivity (WHEI-164 fibrosarcoma and TSA mammary adenocarcinoma). The anti-tumor effects were compared to those induced by free TNF and IL-12. The results show that a) isoDGR/Au/TNF exerts more potent anti-tumor effects than free TNF in the TNF sensitive WHEI-164 model (FIG. 12 A); b) a dose of isoDGR/Au/IL-12 containing 60 pg of IL-12 induces an anti-tumor effect similar to that induced by 15000 pg of free IL-12; c) isoDGR/Au/TNF/IL-12 exerts anti-tumor effects against TSA adenocarcinoma, a TNF resistant tumor.

These findings indicate that isoDGR-tagged gold nanoparticles can be exploited as a versatile platform for single or multi-cytokine delivery to tumors and improve their anti-tumor activity.

The efficacy of cytokines in cancer therapy is often limited by toxicity and counter-regulatory mechanisms. The TNF and isoDGR peptides can be exploited for the preparation of gold nanoparticles that efficiently home to tumors, by virtue of active and passive mechanisms. Targeted gold nanoparticles can then be exploited as a multifunctional platform for the delivery of extremely low, yet pharmacologically active doses of synergistic cytokines to tumors vessels. For example, these nanoparticles can work as an efficient nano-system for the delivery of single or multi-cytokines, such as TNF, IL-12, IFNgamma, EMAP-II to tumor vessels without causing the activation of counter-regulatory mechanisms and toxic reactions.

The isoDGR-tagged gold nanoparticles could be exploited in principle also for the delivery of other biological response modifiers to the tumor microenvironment, such as lipopolysaccharide or other agents capable of inducing TNF and other anticancer cytokines, or for the delivery of antigens capable of eliciting a specific immune response against tumors.

Considering that inflammatory macrophages can express alphavbeta3 (Antov et al., J. Cell. Physiol. 2011; Wilder, Ann Rheum Dis 2002) and that vessels of inflamed tissues can express CD13, i.e. the receptor of NGR (Di Matteo et al, J Histochem Cytochem. 2011), the targeted gold nanoparticles could be used also in other diseases characterized by angiogenesis and inflammation, such as rheumatoid arthritis, type 1 diabetes, graft versus host disease for the delivery, in this case, of immunosuppressive/immunomodulatory compounds (e.g. IL-10) alone or in combination with antigen/s, costimulatory molecules, antibodies ... at the inflammatory site. For instance, in type 1 diabetes one can envisage the delivery to the inflammatory site (i.e., the pancreas) of nanoparticles coated with Abs (e.g., aCD3, aCD2, aCD28 mAbs), immunomodulatory molecules (e.g., IL-10, TGF-b, IL-27) and disease specific antigen/s bound to host-restricted MHC molecules (e.g., insulin, GAD65, ZnT8). This might lead to LOCAL activation and generation of Ag specific T cells with regulatory properties that can reduce inflammation and block autoreactive immune responses.

Example 3

NGR Peptides

Materials and Methods
Cell Lines and Reagents

Human fibrosarcoma (HT-1080) and human breast adenocarcinoma cells (MCF-7) cells were cultured in DMEM containing 10% fetal bovine serum supplemented with 2 mM glutamine, 50 µg/ml streptomycin, 100 U/ml penicillin and 0.25 µg/ml amphotericin-B. Human umbilical vein endothelial cells (HUVECs) (Clonetics, Lonza, Switzerland) were cultured according to the recommended protocols. Amino-modified quantum dots nanoparticles (Qdot), Qdot605 ITK Amino PEG, were from Invitrogen (Carlsbad, Calif.). Sulfosuccinimidyl-4-[N-maleimidomethyl]cyclohexane-1-carboxylate (sulfo-SMCC) and bis[sulfosuccinimidyl]suberate (BS3) were from Pierce (Rockford, Ill.). Human serum albumin (HSA) was from Baxter (Deerfield, Ill.); bovine serum albumin (BSA) was from Sigma. Sodium phosphate buffer (10 mM, pH 7.4), containing 138 mM sodium chloride, 2.7 mM potassium chloride (PBS). Mouse anti-human CD13 monoclonal antibody (mAb WM15) was from Acris (Acris Antibodies, Germany); AlexaFluor 488-goat anti-mouse IgG and 4',6-diamidino-2-phenylindole (DAPI) were from Invitrogen.

25 mM HEPES, pH 7.4 containing 150 mM sodium chloride (HEPES buffer).
Peptide Synthesis and Characterization Five head-to-tail cyclic peptides (see FIG. 13 for schematic representations of each peptide and code) were prepared by the solid-phase Fmoc method.[29] All peptides were dissolved in water and stored in aliquots at −20° C. The molecular mass of each peptide was checked by MALDI-TOF mass spectrometry (see table 4).
Coupling of NGR Peptides to Qdot-Fluorescent Nanoparticles All reactions were performed at room temperature. Qdot (4 nmoles in 440 µl of 25 HEPES buffer containing 5 mM EDTA (HEPES-E) were mixed with sulfo-SMCC (1.38 µmoles in 60 µl of water), left to react for 1 h and purified by gel-filtration chromatography on NAP-5 column (GE Healthcare) pre-equilibrated in HEPES-E, according to the manufacturer's instructions. An aliquot of the activated-Qdot (200 µl containing 0.66 nmoles of Qdot) was mixed with each head-to-tail cyclic peptide (160 µg, in 32 µl of water), or with water alone, and incubated for 2 h. Then, 2-mercaptoethanol was added (0.1 mM, final concentration) and left to incubate for 0.5 h at room temperature. Peptide/Qdot and Qdot nanoparticles activated with sulfo-SMCC but lacking the peptide (Qdot), were then purified by ultrafiltration using an Ultra-4 Ultracel-100K (Amicon, Millipore Corporation, Billerica, Mass.), resuspended 200 µl of HEPES buffer.
Binding Assays of NGR Peptide/Qdot to CD13-Positive and CD13-Negative Cells.

The binding of NGR-peptide/Qdot conjugates to HT-1080, HUVECs and MCF-7, was analyzed as follows: the cells were grown in chamber slides (3-4×10$^4$ cell/well, plated 48 h before the experiment). After washing with DMEM containing 1% fetal bovine serum (binding buffer), each NGR-peptide/Qdot conjugate (3-10 nM, in binding buffer) was added to the cells and left to incubate for 2 h at 37° C. in 5% $CO_2$. After three washings with binding buffer (5 min each), the cells were fixed with 50 mM sodium phosphate buffer, pH 7.3, containing 2% paraformaldehyde, 3% sucrose, 150 mM sodium chloride for 15 min at room temperature. Nuclei were counterstained with DAPI (0.025 µg/ml). The cells were then analyzed using an Axioscop 40 FL microscope (Carl Zeiss, Germany) equipped with Axio-Cam MRc5 digital camera and Axiovison software (Carl Zeiss).
Coupling of c(CNGRGG) (SEQ ID NO:42) Peptide (NGR#3) to Human Serum Albumin.

All reactions were performed at room temperature. HSA (40 mg in 380 µl of HEPES-E) was mixed with sulfo-SMCC (2.4 mg in 120 µl of the same buffer), left to react for 1 h and purified by gel-filtration chromatography on NAP-5 column. Aliquots of activated-HSA were mixed with 1.5 mg of NGR#3 (9:1, peptide/HSA molar ratio) and left to react for 3 h. Then, 2-mercaptoethanol was added (1 mM, final concentration) and left to incubate for 0.5 h. The conjugate was gel-filtered through a PD10 column pre-equilibrated with 25 mM HEPES, 138 mM sodium chloride containing pH 7.4, and stored at −20° C.
Quantification of isoDGR in NGR#3-HSA and NGR-2C Peptide Quantification of isoDGR content in NGR#3-HSA and NGR-2C, before and after forced degradation at 37° C. in various buffers, was measured using a competitive integrin binding assay based on $\alpha v\beta 3$ integrin coated plates essentially as described in the "Materials and Methods" of Example 1. The amount of isoDGR was estimated by interpolating binding data on calibration curves made with the corresponding isoDGR#3-HSA or disulfide-bridged CisoDGRCGVRY (SEQ ID NO:34) peptide (isoDGR-2C). Direct binding assay of NGR#3-HSA or isoDGR#3-HSA to $\alpha v\beta 3$ were also performed using a mouse polyclonal anti-HSA antibody, followed by goat anti-mouse-HRP secondary antibody (Sigma) in the detection step.
Results
Identification of a New NGR Containing Peptide that Binds to CD13-Positive Cells.

We have prepared various head-to-tail cyclized NGR peptides (5-7 residues) containing a Cys residue to facilitate chemical conjugation to aminogroup-containing compounds (FIG. 13). To assess their functional properties we have coupled each peptide to sulfo-SMCC-activated Qdot fluorescent nanoparticles and analyzed their binding to CD13-positive (HT-1080 and HUVECs) and negative cell (MCF-7) cells (FIG. 14A). In parallel, we have also coupled the ac-CNGRCGVRSSSRTPSDKY (SEQ ID NO:33) peptide (ac-NGR-2C-$TNF_{1-11}$), a ligand of CD13-positive cells to BS3-activated Qdot, to be used as a positive control [23].

Fluorescence microscopy experiments showed that both NGR#3-Qdot and ac-NGR-2C-$TNF_{1-11}$/Qdot could bind CD13-positive cells, whereas little or no binding was observed with the other head-to-tail cyclized NGR peptides. NGR#3-Qdot failed to bind CD13-negative MCF-7 cells, suggesting that the binding was related to CD13 expression. (FIG. 14B).

The Molecular Scaffold of NGR#3 Peptide Affects the Deamidation Rate.

It is well known that NGR may undergo Asn deamidation generating isoDGR, an integrin binding motif [25, 47]. To assess whether the molecular scaffold of NGR might affect the deamidation rate we analyzed the molecular masses of NGR#3 and CNGRCGVRY (SEQ ID NO:37) (NGR-2C) before and after incubation at 37° C. in 0.1 M ammonium bicarbonate buffer, pH 8.5 (AmBic) for various times. The results showed that NGR-2C deamidation is faster than that of NGR#3 (FIG. 15). To assess whether the coupling of NGR#3 to proteins could also affect peptide deamidation we coupled NGR#3 to sulfo-SMCC activated HSA (9:1 peptide/protein ratio, NGR#3-HSA) and monitored isoDGR formation by measuring the binding to αvβ3. Biochemical characterization of the conjugate, before incubation, showed that NGR#3-HSA has a hydrodynamic size similar to that of HSA, by gel filtration (FIG. 16A). Furthermore, mass spectrometry analysis of HSA and NGR#3-HSA reveled a molecular mass of 66816 and 70238 Da, respectively, suggesting that NGR#3-HSA consist of monomeric HSA modified with 4-5 NGR#3 peptides (FIG. 16B). Then, we incubated NGR#3-HSA in AmBic, for 16 h at 37° C., a condition that favors Asn deamidation [23, 25] and tested its binding to αvβ3. Heat-treated NGR#3-HSA, but not NGR#3-HSA could bind to αvβ3 (FIG. 17A). The extent of binding of heat-treated NGR-HSA was very similar to that obtained with isoDGR#3-HSA, i.e. a conjugate prepared using a similar peptide having isoAsp in place of Asn (FIG. 17B, right). These results suggest that also NGR#3-HSA can generate isoDGR upon accelerated aging. However, kinetic studies in PBS (pH 7.4) at 37° C. showed that NGR#3-HSA is markedly more stable than NGR-2C (FIG. 17C).

Given the notion that the buffer composition may affect NGR-to-isoDGR transition [23], we then studied the effect of DMEM (pH 7.5) and HEPES buffer (pH, 7.4) on NGR#3-HSA stability after incubation at 37° C. for various times.

The results showed that NGR#3-HSA is markedly more stable in HEPES buffer than in DMEM (FIG. 17D). Thus, HEPES buffer is suitable for preparation and storage of NGR#3 peptide conjugates.

Abbreviations List isoAsp-Gly-Arg (isoDGR); human serum albumin (HSA); avidin (AV); streptavidin (STV); peroxidase, (HRP), gold nanoparticles (Au); tumor necrosis factor-α (TNF-α); Abraxane (abx).

Tables

TABLE 1

Binding of head-to-tail cyclized isoDGR peptides to integrins as measured by competitive binding assay.

| | | Binding of isoDGR/STV-HRP to | | | | | | | | |
|---|---|---|---|---|---|---|---|---|---|---|
| | | αvβ3 | | αvβ5 | | αvβ6 | | αvβ8 | | α5β1 |
| Peptide Head-to-tail cyclized | Code | $n^a$ | $Ki^b$ (nM) | n | Ki (nM) | n | Ki (nM) | n | Ki (nM) | n | Ki (nM) |
| c(CGisoDGRG) (SEQ ID NO: 1) | isoDGR#1 | 13 | 103 ± 18 $(1)^c$ | 9 | 225 ± 57 (2) | 11 | 1470 ± 211 (14) | 10 | 7268 ± 1169 (70) | 9 | 320 ± 49 (3) |
| c(CisoDGRG) (SEQ ID NO: 9) | isoDGR#2 | 2 | 483 ± 212 (1) | 2 | 492 ± 166 (1) | 2 | 899 ± 87 (1.9) | 2 | 1084 ± 432 (2.2) | 2 | 266 ± 59 (0.5) |
| c(CisoDGRGG) (SEQ ID NO: 30) | isoDGR#3 | 7 | 43 ± 9.6 (1) | 4 | 42 ± 17 (1) | 6 | 58 ± 18 (1.3) | 5 | 54 ± 13 (1.2) | 4 | 21 ± 5.1 (0.5) |
| c(CphgisoDGRG)$^e$ (SEQ ID NO: 5) | isoDGR#4 | 1 | 1493 (1) | 1 | 1121 (0.7) | 1 | 45 (0.03) | 1 | 51 (0.03) | 1 | 15 (0.01) |
| c(CGisoDGRphg) (SEQ ID NO: 6) | isoDGR#5 | 5 | 94 ± 27 (1) | 3 | 123 ± 27 (1.30) | 5 | 348 ± 48 (3.7) | 1 | 3966 (42) | 2 | 307 ± 142 (3.26) |
| c(CisoDGRphgG) (SEQ ID NO: 43) | isoDGR#6 | 1 | 272 (1) | 1 | 174 (0.63) | 1 | 219 (0.8) | 1 | 366 (1.34) | 1 | 73 (0.26) |
| c(CisoDGRGphg) (SEQ ID NO: 44) | isoDGR#7 | 1 | 660 (1) | 1 | 433 (0.6) | 1 | 20 (0.03) | 1 | 248 (0.4) | 1 | 27 (0.04) |

$^a$n, number of independent experiments (each in duplicate).
$^b$Ki: equilibrium dissociation constant of the competitor (mean ± SE). Ki was calculated by non-linear regression analysis of competitive binding data by using the "One site - Fit Ki" equation of the GraphPad Prism Software (GraphPad Software, Version 5.00 San Diego, California, USA).
$^c$The number in parenthesis indicates the ratio of integrin Ki/αvβ3 Ki.
$^e$phg: D-phenylglycine.

TABLE 2

Binding of peak 1 (P1) and peak 2 (P2) to integrins as measured by competitive binding assay.

| | | Binding of isoDGR/STV-HRP to | | | | | | | | |
|---|---|---|---|---|---|---|---|---|---|---|
| | | αvβ3 | | αvβ5 | | αvβ6 | | αvβ8 | | α5β1 |
| Peptide | $n^a$ | $Ki^b$ (nM) | n | Ki (nM) | n | Ki (nM) | n | Ki (nM) | n | Ki (nM) |
| isoDGR#1 | | | | | | | | | | |
| isoDGR#1-P1 | 2 | 35 ± 6 (1) | 1 | 35 (1) | 1 | 583 (17) | 2 | 5603 ± 2410 (160) | 1 | 302 (8.6) |

TABLE 2-continued

Binding of peak 1 (P1) and peak 2 (P2) to integrins as measured by competitive binding assay.

| | | | | | Binding of isoDGR/STV-HRP to | | | | | |
|---|---|---|---|---|---|---|---|---|---|---|
| | | αvβ3 | | αvβ5 | | αvβ6 | | αvβ8 | | α5β1 |
| Peptide | n[a] | Ki[b] (nM) | n | Ki (nM) | n | Ki (nM) | n | Ki (nM) | n | Ki (nM) |
| isoDGR#1-P2 | 2 | 33 ± 4.5 (1) | 2 | 52 ± 11 (1.6) | 2 | 2727 ± 194 (80) | 2 | 10487 ± 2120 (318) | 2 | 318 ± 131 (9.6) |
| isoDGR#3 | | | | | | | | | | |
| isoDGR#3-P1 | 2 | 9.4 ± 1.4 (1) | | NA[d] | 1 | 91 (10) | 1 | 131 (14) | | NA |
| isoDGR#3-P2 | 2 | 18 ± 1.9 (1) | | NA | 1 | 468 (26) | 1 | 430 (24) | | NA |

[a]n: number of independent experiments (each in duplicate).
[b]Ki: equilibrium dissociation constant of the competitor (mean ± SEM). Ki was calculated by nonlinear regression analysis of competitive binding data by using the "One site - Fit Ki" equation of the GraphPad Prism Software (GraphPad Software, Version 5.00 San Diego, California, USA).
[c]the number in parenthesis indicates the ratio of integrin Ki/αvβ3 Ki.
[d]NA: not analyzed.

TABLE 3

Binding of isoDGR- albumin or -avidin conjugates to integrins as measured by competitive binding assay.

| | | | | | Binding of isoDGR/STV-HRP to | | | | | |
|---|---|---|---|---|---|---|---|---|---|---|
| Peptide-protein | | αvβ3 | | αvβ5 | | αvβ6 | | αvβ8 | | α5β1 |
| conjugate (Pep:Prot)[a] | n[b] | Ki[c] (nM) | n | Ki (nM) | n | Ki (nM) | n | Ki (nM) | n | Ki (nM) |
| Albumin | | | | | | | | | | |
| isoDGR#1-HSA(2:1) | 2 | 9.4 ± 2.1 (1)[d] | 2 | 50 ± 9 (5.3) | 2 | 2481 ± 503 (264) | 2 | 30668 ± 6729 (3262) | 2 | 1030 ± 246 (109) |
| isoDGR#1-HSA(3:1) | 1 | 15 (1) | 4 | 117 ± 44 (18) | 4 | 4605 ± 1341 (307) | 1 | 68877 (4591) | 4 | 851 ± 226 (57) |
| isoDGR#1-HSA(9:1) | 2 | 5.3 ± 1.1 (1) | 4 | 19 ± 2.8 (3.6) | 5 | 1316 ± 185 (248) | 2 | 16049 ± 1959 (3028) | 4 | 479 ± 136 (90) |
| isoDGR#3-HSA(2:1) | 4 | 3.5 ± 1 (1) | 3 | 22 ± 15 (6.3) | 2 | 124 ± 52 (35) | 2 | 101 ± 17 (29) | 2 | 112 ± 11 (32) |
| isoDGR#5-HSA(2:1) | 3 | 10 ± 5 (1) | 3 | 31 ± 12 (3) | 2 | 1047 ± 716 (105) | 1 | 10666 (1067) | 2 | 174 ± 45 (17.5) |
| *HSA(0:1) | 2 | >>10000[e] | 2 | >>10000 | 2 | >>10000 | 2 | >>10000 | 2 | >>10000 |
| Avidin | | | | | | | | | | |
| isoDGR#1-AV(9:1) | 3 | 1 ± 0.2 (1) | 1 | 3.9 (3.9) | 3 | 23 ± 4 (23) | 3 | 382 ± 27 (382) | 2 | 96 ± 5 (96) |
| *AV(0:1) | 3 | >>2500 | 3 | >>2500 | 3 | >>2500 | 3 | 1459 ± 659 | 1 | >>2500 |
| Cilengitide[e] | 4 | 0.99 ± 0.14 (1) | 5 | 0.76 ± 0.16 (0.76) | 4 | 50.1 ± 25 (51) | 4 | 121 ± 15 (122) | 3 | 3.24 ± 1.38 (3.3) |

[a]Pep:Prot, mol of peptide/mol of activated protein.
[b]n: number of independent experiments (each in duplicate).
[c]Ki: equilibrium dissociation constant of the competitor (mean ± SEM). Ki was calculated by nonlinear regression analysis of competitive binding data by using the "One site - Fit Ki" equation of the GraphPad Prism Software (GraphPad Software, Version 5.00 San Diego, California, USA).
[d]Ratio of integrin Ki/αvβ3 Ki.
[e]>>, maximum concentration tested, which gave no inhibition.
[f]Cilengitide: cyclo(arginylglycyl-aspartyl-D-phenylalanyl-N-methyl-valyl), an RGD head-to-tail cyclic pentapeptide specific for αvβ3 and αvβ5.

TABLE 4

Molecular mass of NGR cyclic peptides as determined by mass spectrometry analysis.

| Peptide [a] | Code | Expected (Da) | Found (Da) |
|---|---|---|---|
| Head-to-tail cyclic | | | |
| c(CGNGRG) (SEQ ID NO: 13) | NGR#1 | 545.22 | 545.23 |
| c(CNGRG) (SEQ ID NO: 19) | NGR#2 | 488.21 | 488.21 |
| c(CNGRGG) (SEQ ID NO: 45) | NGR#3 | 545.23 | 545.24 |
| c(CPNGRG) (SEQ ID NO: 12) | NGR#4 | 585.26 | 585.28 |
| c(CPNGRGG) (SEQ ID NO: 38) | NGR#5 | 624.28 | 624.27 |
| c(CisoDGRGG) (SEQ ID NO: 30) | isoDGR#3 | 546.21 | 546.19 |
| Disulfide-bridged | | | |
| CNGRCGVRY (SEQ ID NO: 37) | NGR-2C | 1025.43 | 1025.28 |

[a] capital letters: L-aminoacids (single letter code).

REFERENCES

1. Peters T (1996) All About Albumin: Biochemistry, Genetics, and Medical Applications. Academic Press, San Diego, Calif.
2. Stehle G, Sinn H, Wunder A, Schrenk H H, Stewart J C, Hartung G, Maier-Borst W, Heene D L (1997) Plasma protein (albumin) catabolism by the tumor itself—implications for tumor metabolism and the genesis of cachexia. Crit Rev Oncol Hematol 2:77-100.
3. Kratz F (2008) Albumin as a drug carrier: design of prodrugs, drug conjugates and nanoparticles. J Control Release 3:171-183.
4. Elsadek B, Kratz F (2011) Impact of albumin on drug delivery—New applications on the horizon. J Control Release.
5. Hartung G, Stehle G, Sinn H, Wunder A, Schrenk H H, Heeger S, Kranzle M, Edler L, Frei E, Fiebig H H, Heene D L, Maier-Borst W, Queisser W (1999) Phase I trial of methotrexate-albumin in a weekly intravenous bolus regimen in cancer patients. Phase I Study Group of the Association for Medical Oncology of the German Cancer Society. Clin Cancer Res 4:753-759.
6. Vis A N, van der Gaast A, van Rhijn B W, Catsburg T K, Schmidt C, Mickisch G H (2002) A phase II trial of methotrexate-human serum albumin (MTX-HSA) in patients with metastatic renal cell carcinoma who progressed under immunotherapy. Cancer Chemother Pharmacol 4:342-345.
7. Gradishar W J, Tjulandin S, Davidson N, Shaw H, Desai N, Bhar P, Hawkins M, O'Shaughnessy J (2005) Phase III trial of nanoparticle albumin-bound paclitaxel compared with polyethylated castor oil-based paclitaxel in women with breast cancer. J Clin Oncol 31:7794-7803.
8. Gradishar W J, Krasnojon D, Cheporov S, Makhson A N, Manikhas G M, Clawson A, Bhar P (2009) Significantly longer progression-free survival with nab-paclitaxel compared with docetaxel as first-line therapy for metastatic breast cancer. J Clin Oncol 22:3611-3619.
9. Unger C, Haring B, Medinger M, Drevs J, Steinbild S, Kratz F, Mross K (2007) Phase I and pharmacokinetic study of the (6-maleimidocaproyl)hydrazone derivative of doxorubicin. Clin Cancer Res 16:4858-4866.
10. Desgrosellier J S, Cheresh D A (2009) Integrins in cancer: biological implications and therapeutic opportunities. Nat Rev Cancer 1:9-22.
11. Avraamides C J, Garmy-Susini B, Varner J A (2008) Integrins in angiogenesis and lymphangiogenesis. Nat Rev Cancer 8:604-617.
12. Barczyk M, Carracedo S, Gullberg D (2010) Integrins. Cell Tissue Res 1:269-280.
13. Dechantsreiter M A, Planker E, Matha B, Lohof E, Holzemann G, Jonczyk A, Goodman S L, Kessler H (1999) N-Methylated cyclic RGD peptides as highly active and selective alpha(V)beta(3) integrin antagonists. J Med Chem 16:3033-3040.
14. Mas-Moruno C, Rechenmacher F, Kessler H (2010) Cilengitide: the first anti-angiogenic small molecule drug candidate design, synthesis and clinical evaluation. Anticancer Agents Med Chem 10:753-768.
15. Chen K, Xie J, Chen X (2009) RGD-human serum albumin conjugates as efficient tumor targeting probes. Mol Imaging 2:65-73.
16. Temming K, Meyer D L, Zabinski R, Dijkers E C, Poelstra K, Molema G, Kok R J (2006) Evaluation of RGD-targeted albumin carriers for specific delivery of auristatin E to tumor blood vessels. Bioconjug Chem 6:1385-1394.
17. Temming K, Lacombe M, Schaapveld R Q, Orfi L, Keri G, Poelstra K, Molema G, Kok R J (2006) Rational design of RGD-albumin conjugates for targeted delivery of the VEGF-R kinase inhibitor PTK787 to angiogenic endothelium. ChemMedChem 11:1200-1203.
18. Temming K, Schiffelers R M, Molema G, Kok R J (2005) RGD-based strategies for selective delivery of therapeutics and imaging agents to the tumour vasculature. Drug Resist Updat 6:381-402.
19. Curnis F, Gasparri A, Sacchi A, Longhi R, Corti A (2004) Coupling tumor necrosis factor-alpha with alphaV integrin ligands improves its antineoplastic activity. Cancer Res 2:565-571.
20. Liu Z, Wang F, Chen X (2008) Integrin alpha(v) beta (3)-Targeted Cancer Therapy. Drug Dev Res 6:329-339.
21. Schottelius M, Laufer B, Kessler H, Wester H J (2009) Ligands for mapping alphavbeta3-integrin expression in vivo. Acc Chem Res 7:969-980.
22. Tarrus M, van der Sloot A M, Temming K, Lacombe M, Opdam F, Quax W J, Molema G, Poelstra K, Kok R J (2008) RGD-avidin-biotin pretargeting to alpha v beta 3 integrin enhances the proapoptotic activity of TNF alpha related apoptosis inducing ligand (TRAIL). Apoptosis 2:225-235.
23. Curnis F, Cattaneo A, Longhi R, Sacchi A, Gasparri A M, Pastorino F, Di Matteo P, Traversari C, Bachi A, Ponzoni M, Rizzardi G P, Corti A (2010) Critical role of flanking residues in NGR-to-isoDGR transition and CD13/integrin receptor switching. J Biol Chem 2010; 285(12):9114-9123.
24. Spitaleri A, Mari S, Curnis F, Traversari C, Longhi R, Bordignon C, Corti A, Rizzardi G P, Musco G (2008) Structural basis for the interaction of isoDGR with the RGD-binding site of alphavbeta3 integrin. J Biol Chem 28:19757-19768.
25. Curnis F, Longhi R, Crippa L, Cattaneo A, Dondossola E, Bachi A, Corti A (2006) Spontaneous formation of L-isoaspartate and gain of function in fibronectin. J Biol Chem 2006; 281(47):36466-36476.

26. Frank A O, Otto E, Mas-Moruno C, Schiller H B, Marinelli L, Cosconati S, Bochen A, Vossmeyer D, Zahn G, Stragies R, Novellino E, Kessler H (2010) Conformational control of integrin-subtype selectivity in isoDGR peptide motifs: a biological switch. Angew Chem Int Ed Engl 48:9278-9281.
27. Curnis F, Sacchi A, Gasparri A, Longhi R, Bachi A, Doglioni C, Bordignon C, Traversari C, Rizzardi G, Corti A (2008) Isoaspartate-Glycine-Arginine: A New Tumor Vasculature-Targeting Motif. Cancer Res 17:7073-7082.
28. Curnis F, Gasparri A, Sacchi A, Cattaneo A, Magni F, Corti A (2005) Targeted delivery of IFNgamma to tumor vessels uncouples antitumor from counterregulatory mechanisms. Cancer Res 7:2906-2913.
29. Fields G B, Noble R L (1990) Solid phase peptide synthesis utilizing 9-fluorenylmethoxycarbonyl amino acids. Int J Pept Protein Res 1990; 35(3):161-214.
30. Gasparri A, Moro M, Curnis F, Sacchi A, Pagano S, Veglia F, Casorati G, Siccardi A G, Dellabona P, Corti A (1999) Tumor pretargeting with avidin improves the therapeutic index of biotinylated tumor necrosis factor alpha in mouse models. Cancer Res 12:2917-2923.
31. Brooks P C, Montgomery A M, Rosenfeld M, Reisfeld R A, Hu T, Klier G, Cheresh D A (1994) Integrin alpha v beta 3 antagonists promote tumor regression by inducing apoptosis of angiogenic blood vessels. Cell 7:1157-1164.
32. Hammes H P, Brownlee M, Jonczyk A, Sutter A, Preissner K T (1996) Subcutaneous injection of a cyclic peptide antagonist of vitronectin receptor-type integrins inhibits retinal neovascularization. Nat Med 5:529-533.
33. Brooks P C, Stromblad S, Klemke R, Visscher D, Sarkar F H, Cheresh D A (1995) Antiintegrin alpha v beta 3 blocks human breast cancer growth and angiogenesis in human skin. J Clin Invest 4:1815-1822.
34. Giljohann D A, Seferos D S, Daniel W L, Massich M D, Patel P C, Mirkin C A (2010) Gold nanoparticles for biology and medicine. Angew Chem Int Ed Engl 19:3280-3294.
35. Cai W, Gao T, Hong H, Sun J (2008) Applications of gold nanoparticles in cancer nanotechnology. Nanotechnology, Science and Applications 1:17-32.
36. Libutti S K, Paciotti G F, Byrnes A A, Alexander B R, Jr., Gannon W E, Walker M, Seidel G D, Yuldasheva N, Tamarkin L (2010) Phase I and pharmacokinetic studies of CYT-6091, a novel PEGylated colloidal gold-rhTNF nanomedicine. Clin Cancer Res 24:6139-6149.
37. Lejeune F J, Lienard D, Matter M, Ruegg C (2006) Efficiency of recombinant human TNF in human cancer therapy. Cancer Immun: 6.
38. Balkwill F (2009) Tumour necrosis factor and cancer. Nat Rev Cancer 5:361-371.
39. Pathuri G, Sahoo K, Awasthi V, Gali H (2010) Synthesis and in vivo evaluation of Tc-99m-labeled cyclic CisoDGRC peptide conjugates for targeting alphavbeta3 integrin expression. Bioorg Med Chem Lett 20:5969-5972.
40. Reardon D A, Neyns B, Weller M, Tonn J C, Nabors L B, Stupp R (2011) Cilengitide: an RGD pentapeptide alphanubeta3 and alphanubeta5 integrin inhibitor in development for glioblastoma and other malignancies. Future Oncol 3:339-354.
41. Zhu J, Motejlek K, Wang D, Zang K, Schmidt A, Reichardt L F (2002) beta8 integrins are required for vascular morphogenesis in mouse embryos. Development 12:2891-2903.
42. Cambier S, Mu D Z, O'Connell D, Boylen K, Travis W, Liu W H, Broaddus V C, Nishimura S L (2000) A role for the integrin alphavbeta8 in the negative regulation of epithelial cell growth. Cancer Res 24:7084-7093.
43. Lakhe-Reddy S, Khan S, Konieczkowski M, Jarad G, Wu K L, Reichardt L F, Takai Y, Bruggeman L A, Wang B, Sedor J R, Schelling J R (2006) Beta8 integrin binds Rho GDP dissociation inhibitor-1 and activates Rac1 to inhibit mesangial cell myofibroblast differentiation. J Biol Chem 28:19688-19699.
44. Chernousov M A, Carey D J (2003) alphaVbeta8 integrin is a Schwann cell receptor for fibrin. Exp Cell Res 2:514-524.
45. Sheppard D, Rozzo C, Starr L, Quaranta V, Erie D J, Pytela R (1990) Complete amino acid sequence of a novel integrin beta subunit (beta 6) identified in epithelial cells using the polymerase chain reaction. J Biol Chem 20:11502-11507.
46. Curnis, F., and Corti, A. (2004) *Methods Mol Med* 98, 9-22
47. Corti A, Curnis F. Isoaspartate-dependent molecular switches for integrin-ligand recognition. J Cell Sci 2011; 124(Pt 4): 515-22.

The invention claimed is:

1. A product comprising a cyclic hexapeptide comprising the sequence XX'isoDGRX" (SEQ ID NO:11), wherein X is selected from the group consisting of G, C and phG; wherein X' is selected from the group consisting of G, C and phG, wherein X" is selected from the group consisting of G and phG, wherein the hexapeptide is cyclized by joining the N- and C-termini of its main chain, and wherein the cyclic peptide is joined to albumin.

2. The product according to claim 1 wherein the peptide comprises an amino acid suitable for conjugation to the albumin in addition to the residues isoDGR of SEQ ID NO: 11.

3. The product according to claim 2 wherein the amino acid suitable for conjugation is conjugated to the albumin via its side chain.

4. The product according to claim 1, wherein the cyclic hexapeptide comprises cyclic CGisoDGRG (SEQ ID NO:1), cyclic GCisoDGRG (SEQ ID NO:4), cyclic CphGisoDGRG (SEQ ID NO:5), cyclic CGisoDGRphG (SEQ ID NO:6), cyclic GCisoDGRphG (SEQ ID NO:7) or cyclic phGCisoDGRG (SEQ ID NO:8).

5. The product according to claim 1 wherein the albumin is human serum albumin.

6. The product according to claim 1 wherein the peptide and albumin are joined via a cross-linker.

7. The product according to claim 1 wherein the product further comprises an effector domain.

8. The product according to claim 7 wherein the effector domain is selected from the group consisting of a drug, an imaging compound, a nanoparticle, a nanoparticle:drug complex, a nanoparticle:imaging compound complex, avidin, neutravidin and streptavidin.

9. The product according to claim 8, wherein the effector domain is a nanoparticle:drug complex and wherein the nanoparticle:drug complex comprises one or more cytokines.

10. The product according to claim 8 wherein the nanoparticle is a gold nanoparticle.

11. A pharmaceutical composition comprising a pharmaceutically effective amount of product according to claim 1.

12. A method of inhibiting tumor growth comprising administering a product according to claim 1.

* * * * *

SEQUENCE LISTING

```
<160> NUMBER OF SEQ ID NOS: 45

<210> SEQ ID NO 1
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MOD_RES
<222> LOCATION: (3)..(3)
<223> OTHER INFORMATION: Isoaspartic acid

<400> SEQUENCE: 1

Cys Gly Asp Gly Arg Gly
1               5
```

```
<210> SEQ ID NO 2
<211> LENGTH: 5
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MOD_RES
<222> LOCATION: (2)..(2)
<223> OTHER INFORMATION: Isoaspartic acid

<400> SEQUENCE: 2

Cys Asp Gly Arg Cys
1               5

<210> SEQ ID NO 3
<211> LENGTH: 6
<212> TYPE: PRT
<213> ORGANISM: Artificial Sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa may be Gly, Cys or D-phenylglycine
<220> FEATURE:
<221> NAME/KEY: MISC_FEATURE
<222> LOCATION: (2)..(2)
<223> OTHER INFORMATION: Xaa may be Gly, Cys or D-phenylglycine
<220> FEATURE:
<221> NAME/KEY: MISC_FEATURE
<222> LOCATION: (6)..(6)
<223> OTHER INFORMATION: Xaa may be Gly or D-phenylglycine

<400> SEQUENCE: 3

Xaa Xaa Asp Gly Arg Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MOD_RES
<222> LOCATION: (3)..(3)
<223> OTHER INFORMATION: Isoaspartic acid

<400> SEQUENCE: 4

Gly Cys Asp Gly Arg Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (2)..(2)
<223> OTHER INFORMATION: Xaa is D-phenylglycine
<220> FEATURE:
```

```
<221> NAME/KEY: MOD_RES
<222> LOCATION: (3)..(3)
<223> OTHER INFORMATION: Isoaspartic acid

<400> SEQUENCE: 5

Cys Xaa Asp Gly Arg Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MOD_RES
<222> LOCATION: (3)..(3)
<223> OTHER INFORMATION: Isoaspartic acid
<220> FEATURE:
<221> NAME/KEY: MISC_FEATURE
<222> LOCATION: (6)..(6)
<223> OTHER INFORMATION: Xaa is D-phenylglycine

<400> SEQUENCE: 6

Cys Gly Asp Gly Arg Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MOD_RES
<222> LOCATION: (3)..(3)
<223> OTHER INFORMATION: Isoaspartic acid
<220> FEATURE:
<221> NAME/KEY: MOD_RES
<222> LOCATION: (6)..(6)
<223> OTHER INFORMATION: Xaa is D-phenylglycine

<400> SEQUENCE: 7

Gly Cys Asp Gly Arg Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: Xaa is D-phenylglycine
<220> FEATURE:
<221> NAME/KEY: MOD_RES
<222> LOCATION: (3)..(3)
<223> OTHER INFORMATION: Isoaspartic acid

<400> SEQUENCE: 8

Xaa Cys Asp Gly Arg Gly
```

```
1               5

<210> SEQ ID NO 9
<211> LENGTH: 5
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MOD_RES
<222> LOCATION: (2)..(2)
<223> OTHER INFORMATION: Isoaspartic acid

<400> SEQUENCE: 9

Cys Asp Gly Arg Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa may be Gly, Cys or D-phenylglycine
<220> FEATURE:
<221> NAME/KEY: MISC_FEATURE
<222> LOCATION: (2)..(2)
<223> OTHER INFORMATION: Xaa may be Gly, Cys or D-phenylglycine
<220> FEATURE:
<221> NAME/KEY: MISC_FEATURE
<222> LOCATION: (6)..(6)
<223> OTHER INFORMATION: Xaa may be Gly D-phenylglycine

<400> SEQUENCE: 10

Xaa Xaa Asn Gly Arg Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa may be Gly, Cys or D-phenylglycine
<220> FEATURE:
<221> NAME/KEY: MISC_FEATURE
<222> LOCATION: (2)..(2)
<223> OTHER INFORMATION: Xaa may be Gly, Cys or D-phenylglycine
<220> FEATURE:
<221> NAME/KEY: MISC_FEATURE
<222> LOCATION: (6)..(6)
<223> OTHER INFORMATION: Xaa may be Gly or D-phenylglycine

<400> SEQUENCE: 11

Xaa Xaa Asp Gly Arg Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: Cyclic synthetic peptide
```

```
<220> FEATURE:
<221> NAME/KEY: MISC_FEATURE
<223> OTHER INFORMATION: Cyclic peptide

<400> SEQUENCE: 12

Cys Pro Asn Gly Arg Gly
1               5

<210> SEQ ID NO 13
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide

<400> SEQUENCE: 13

Cys Gly Asn Gly Arg Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide

<400> SEQUENCE: 14

Gly Cys Asn Gly Arg Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (2)..(2)
<223> OTHER INFORMATION: Xaa is D-phenylglycine

<400> SEQUENCE: 15

Cys Xaa Asn Gly Arg Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (6)..(6)
<223> OTHER INFORMATION: Xaa is D-phenylglycine

<400> SEQUENCE: 16

Cys Gly Asn Gly Arg Xaa
```

```
1               5

<210> SEQ ID NO 17
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (6)..(6)
<223> OTHER INFORMATION: Xaa is D-phenylglycine

<400> SEQUENCE: 17

Gly Cys Asn Gly Arg Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: Xaa is D-phenylglycine

<400> SEQUENCE: 18

Xaa Cys Asn Gly Arg Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide

<400> SEQUENCE: 19

Cys Asn Gly Arg Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide

<400> SEQUENCE: 20

Cys Gly Asp Gly Arg Gly
1               5

<210> SEQ ID NO 21
<211> LENGTH: 6
<212> TYPE: PRT
<213> ORGANISM: Artificial Sequence
```

```
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide

<400> SEQUENCE: 21

Gly Cys Asp Gly Arg Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (2)..(2)
<223> OTHER INFORMATION: Xaa is D-phenylglycine

<400> SEQUENCE: 22

Cys Xaa Asp Gly Arg Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (6)..(6)
<223> OTHER INFORMATION: Xaa is D-phenylglycine

<400> SEQUENCE: 23

Cys Gly Asp Gly Arg Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (6)..(6)
<223> OTHER INFORMATION: Xaa is D-phenylglycine

<400> SEQUENCE: 24

Gly Cys Asp Gly Arg Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
```

```
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: Xaa is D-phenylglycine

<400> SEQUENCE: 25

Xaa Cys Asp Gly Arg Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide

<400> SEQUENCE: 26

Cys Asp Gly Arg Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide

<400> SEQUENCE: 27

Cys Asn Gly Arg Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Cys Asp Gly Arg Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Isoaspartic acid

<400> SEQUENCE: 29

Cys Asp Gly Arg Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Cyclic synthetic peptide
<220> FEATURE:
```

```
<221> NAME/KEY: MISC_FEATURE
<223> OTHER INFORMATION: Cyclic peptide
<220> FEATURE:
<221> NAME/KEY: MOD_RES
<222> LOCATION: (2)..(2)
<223> OTHER INFORMATION: Isoaspartic acid

<400> SEQUENCE: 30

Cys Asp Gly Arg Gly Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Gly Asn Gly Arg Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide

<400> SEQUENCE: 32

Cys Asn Gly Arg Cys
1               5

<210> SEQ ID NO 33
<211> LENGTH: 18
<212> TYPE: PRT
<213> ORGANISM: Artificial Sequence
<220> FEATURE:
<223> OTHER INFORMATION: Disulphide constrained NGR synthetic peptide
<220> FEATURE:
<221> NAME/KEY: MISC_FEATURE
<222> LOCATION: (1)..(1)
<223> OTHER INFORMATION: Acetylated

<400> SEQUENCE: 33

Cys Asn Gly Arg Cys Gly Val Arg Ser Ser Ser Arg Thr Pro Ser Asp
1               5                   10                  15

Lys Tyr

<210> SEQ ID NO 34
<211> LENGTH: 9
<212> TYPE: PRT
<213> ORGANISM: Artificial Sequence
<220> FEATURE:
<223> OTHER INFORMATION: Disulphide constrained synthetic peptide
<220> FEATURE:
<221> NAME/KEY: MOD_RES
<222> LOCATION: (2)..(2)
<223> OTHER INFORMATION: Isoaspartic acid

<400> SEQUENCE: 34

Cys Asp Gly Arg Cys Gly Val Arg Tyr
1               5

<210> SEQ ID NO 35
<211> LENGTH: 9
<212> TYPE: PRT
<213> ORGANISM: Artificial Sequence
```

<220> FEATURE:
<223> OTHER INFORMATION: Disulphide constrained synthetic peptide
<220> FEATURE:
<221> NAME/KEY: MISC_FEATURE
<222> LOCATION: (1)..(1)
<223> OTHER INFORMATION: Acetylated
<220> FEATURE:
<221> NAME/KEY: MOD_RES
<222> LOCATION: (2)..(2)
<223> OTHER INFORMATION: Isoaspartic acid

<400> SEQUENCE: 35

Cys Asp Gly Arg Cys Gly Val Arg Tyr
1               5

<210> SEQ ID NO 36
<211> LENGTH: 18
<212> TYPE: PRT
<213> ORGANISM: Artificial Sequence
<220> FEATURE:
<223> OTHER INFORMATION: Biotinylated synthetic peptide
<220> FEATURE:
<221> NAME/KEY: MISC_FEATURE
<222> LOCATION: (1)..(1)
<223> OTHER INFORMATION: Acetylated
<220> FEATURE:
<221> NAME/KEY: MOD_RES
<222> LOCATION: (2)..(2)
<223> OTHER INFORMATION: Isoaspartic acid

<400> SEQUENCE: 36

Cys Asp Gly Arg Cys Gly Val Arg Ser Ser Ser Arg Thr Pro Ser Asp
1               5                   10                  15

Lys Tyr

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Cys Asn Gly Arg Cys Gly Val Arg Tyr
1               5

<210> SEQ ID NO 38
<211> LENGTH: 7
<212> TYPE: PRT
<213> ORGANISM: Artificial Sequence
<220> FEATURE:
<223> OTHER INFORMATION: Cyclic synthetic peptide
<220> FEATURE:
<221> NAME/KEY: MISC_FEATURE
<223> OTHER INFORMATION: Cyclic peptide

<400> SEQUENCE: 38

Cys Pro Asn Gly Arg Gly Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 may be Gly, Cys or

```
            D-phenylglycine
<220> FEATURE:
<221> NAME/KEY: MISC_FEATURE
<222> LOCATION: (2)..(2)
<223> OTHER INFORMATION: Xaa in position 2 may be Gly, Cys or
      D-phenylglycine
<220> FEATURE:
<221> NAME/KEY: MISC_FEATURE
<222> LOCATION: (3)..(3)
<223> OTHER INFORMATION: Asp at position 3 is Isoaspartic acid
<220> FEATURE:
<221> NAME/KEY: MISC_FEATURE
<222> LOCATION: (6)..(6)
<223> OTHER INFORMATION: Xaa in position 6 may be Gly or D-phenylglycine

<400> SEQUENCE: 39

Xaa Xaa Asp Gly Arg Xaa
1               5

<210> SEQ ID NO 40
<211> LENGTH: 7
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (2)..(2)
<223> OTHER INFORMATION: Xaa is D-phenylglycine

<400> SEQUENCE: 40

Cys Xaa Gly Asp Gly Arg Gly
1               5

<210> SEQ ID NO 41
<211> LENGTH: 7
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: Xaa is D-phenylglycine

<400> SEQUENCE: 41

Xaa Gly Cys Asp Gly Arg Gly
1               5

<210> SEQ ID NO 42
<211> LENGTH: 6
<212> TYPE: PRT
<213> ORGANISM: Artificial Sequence
<220> FEATURE:
<223> OTHER INFORMATION: Cyclic peptide

<400> SEQUENCE: 42

Cys Asn Gly Arg Gly Gly
1               5

<210> SEQ ID NO 43
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (2)..(2)
<223> OTHER INFORMATION: The Asp at position 2 is Isoaspartic acid
<220> FEATURE:
```

```
<221> NAME/KEY: MISC_FEATURE
<222> LOCATION: (5)..(5)
<223> OTHER INFORMATION: Xaa at position 5 is De-phenylglycine

<400> SEQUENCE: 43

Cys Asp Gly Arg Xaa Gly
1               5

<210> SEQ ID NO 44
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (2)..(2)
<223> OTHER INFORMATION: The Asp at position 2 is Isoaspartic acid
<220> FEATURE:
<221> NAME/KEY: MISC_FEATURE
<222> LOCATION: (6)..(6)
<223> OTHER INFORMATION: Xaa at position 6 is D-phenylglycine

<400> SEQUENCE: 44

Cys Asp Gly Arg Gly Xaa
1               5

<210> SEQ ID NO 45
<211> LENGTH: 6
<212> TYPE: PRT
<213> ORGANISM: Artificial Sequence
<220> FEATURE:
<223> OTHER INFORMATION: Cyclic peptide

<400> SEQUENCE: 45

Cys Asn Gly Arg Gly Gly
1               5
```